(12) United States Patent
Tortschanoff et al.

(10) Patent No.: US 11,193,885 B2
(45) Date of Patent: Dec. 7, 2021

(54) GAS SENSOR

(71) Applicant: Infineon Technologies AG, Neubiberg (DE)

(72) Inventors: Andreas Tortschanoff, Villach (AT); Cristina Consani, Villach (AT); Thomas Grille, Villach (AT); Peter Irsigler, Obernberg/Inn (AT); Christian Ranacher, Gaimberg (AT)

(73) Assignee: INFINEON TECHNOLOGIES AG, Neubiberg (DE)

( * ) Notice: Subject to any disclaimer, the term of this patent is extended or adjusted under 35 U.S.C. 154(b) by 6 days.

(21) Appl. No.: 16/803,031

(22) Filed: Feb. 27, 2020

(65) Prior Publication Data

US 2020/0284721 A1 Sep. 10, 2020

(30) Foreign Application Priority Data

Mar. 8, 2019 (EP) .................................... 19161699

(51) Int. Cl.
*G01J 5/02* (2006.01)
*G01N 21/3504* (2014.01)
*G01N 33/00* (2006.01)

(52) U.S. Cl.
CPC ..... *G01N 21/3504* (2013.01); *G01N 33/0027* (2013.01); *G01N 2201/061* (2013.01); *G01N 2201/0686* (2013.01)

(58) Field of Classification Search
CPC ....... G01N 33/0027; G01N 2201/0686; G01N 2021/0112; G01N 21/3504; G01N 2201/061; G01N 21/01
See application file for complete search history.

(56) References Cited

U.S. PATENT DOCUMENTS

| 4,780,613 | A | * | 10/1988 | Berstein | .................. G01J 3/108 250/343 |
| 5,747,808 | A | | 5/1998 | Wong | |
| 5,861,545 | A | * | 1/1999 | Wood | ................... G01N 21/171 73/23.31 |
| 2006/0285114 | A1 | | 12/2006 | Cao et al. | |
| 2016/0139038 | A1 | * | 5/2016 | Oldsen | ............... G01N 21/0303 356/454 |
| 2017/0343419 | A1 | | 11/2017 | Hopper et al. | |

FOREIGN PATENT DOCUMENTS

WO 2015104133 A1 7/2015

* cited by examiner

*Primary Examiner* — Kiho Kim
(74) *Attorney, Agent, or Firm* — Slater Matsil, LLP

(57) ABSTRACT

In accordance with an embodiment, a gas sensor includes a substrate having a cavity for providing an optical interaction path; a thermal emitter configured to emit broadband IR radiation; a wavelength selective structure configured to filter the broadband IR radiation emitted by the thermal emitter; and an IR detector configured to provide a detector output signal based on a strength of the filtered IR radiation having traversed the optical interaction path.

20 Claims, 20 Drawing Sheets

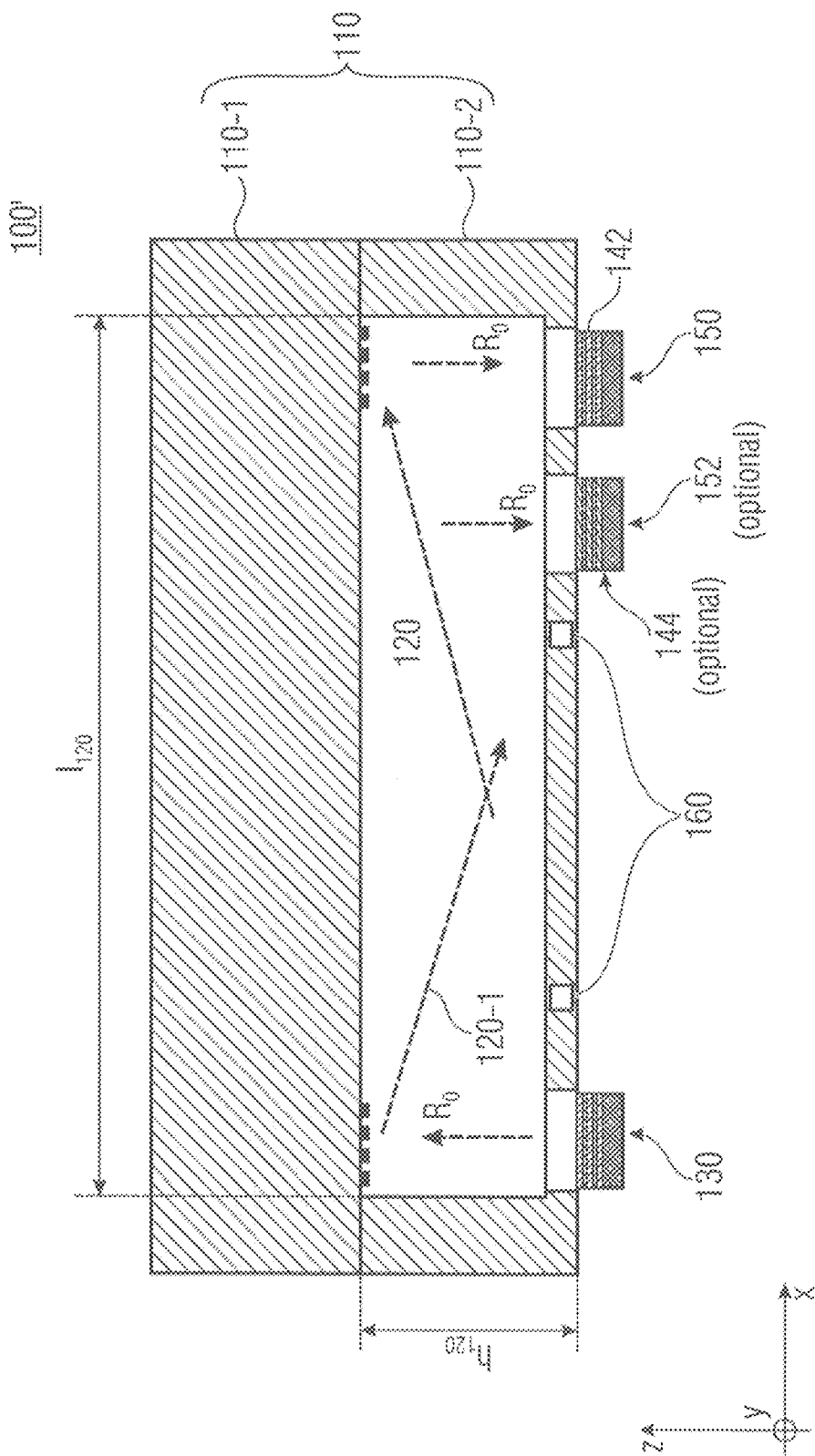

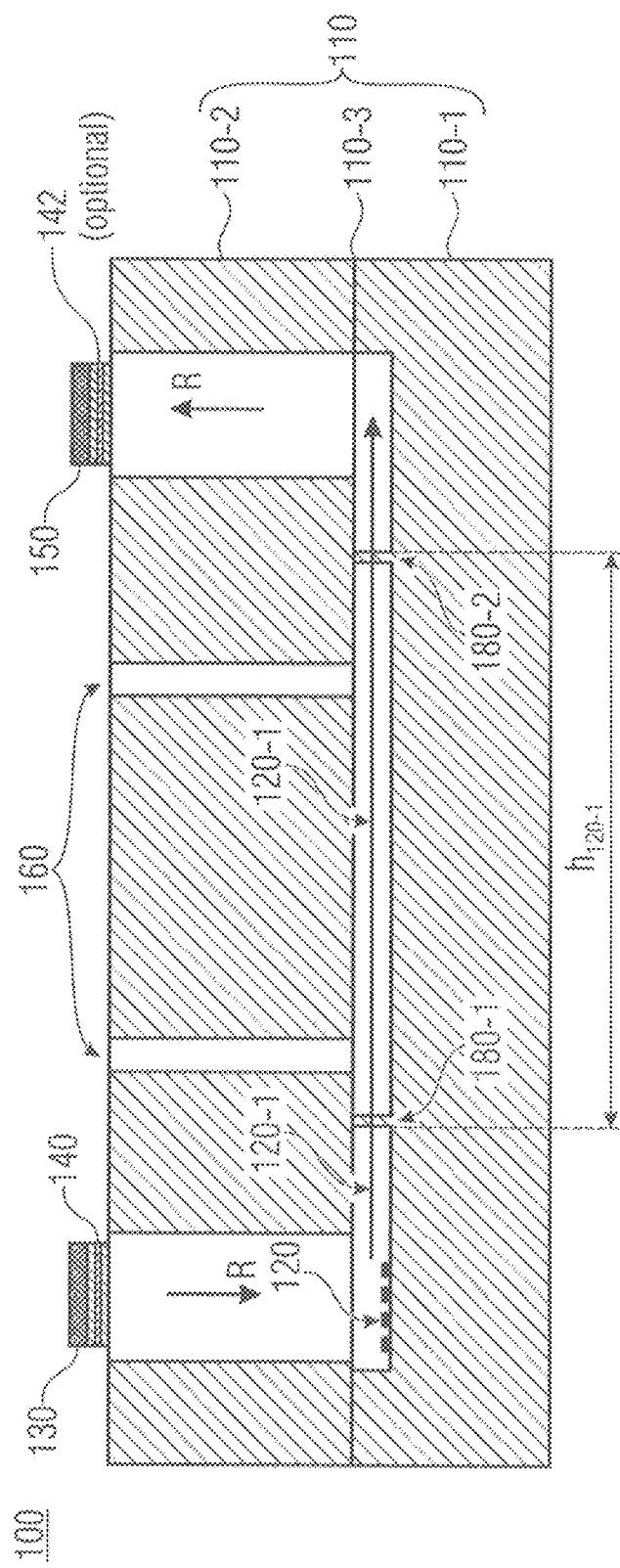
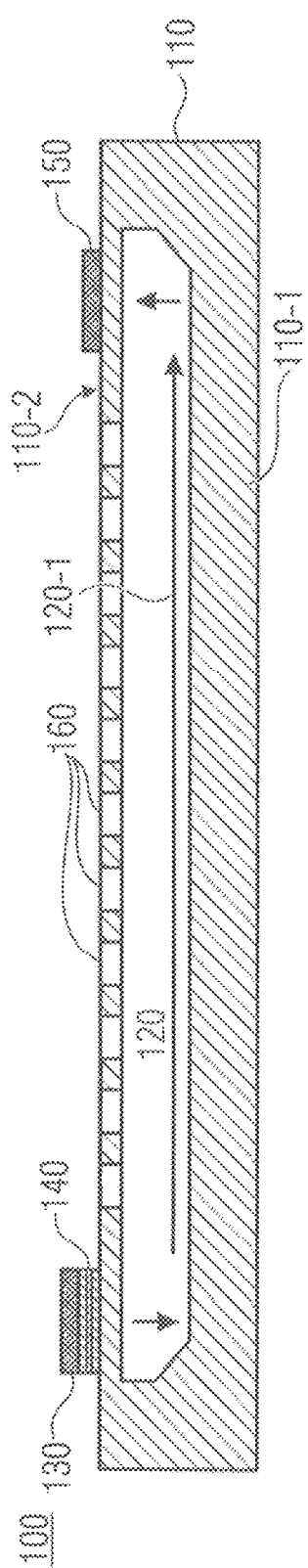

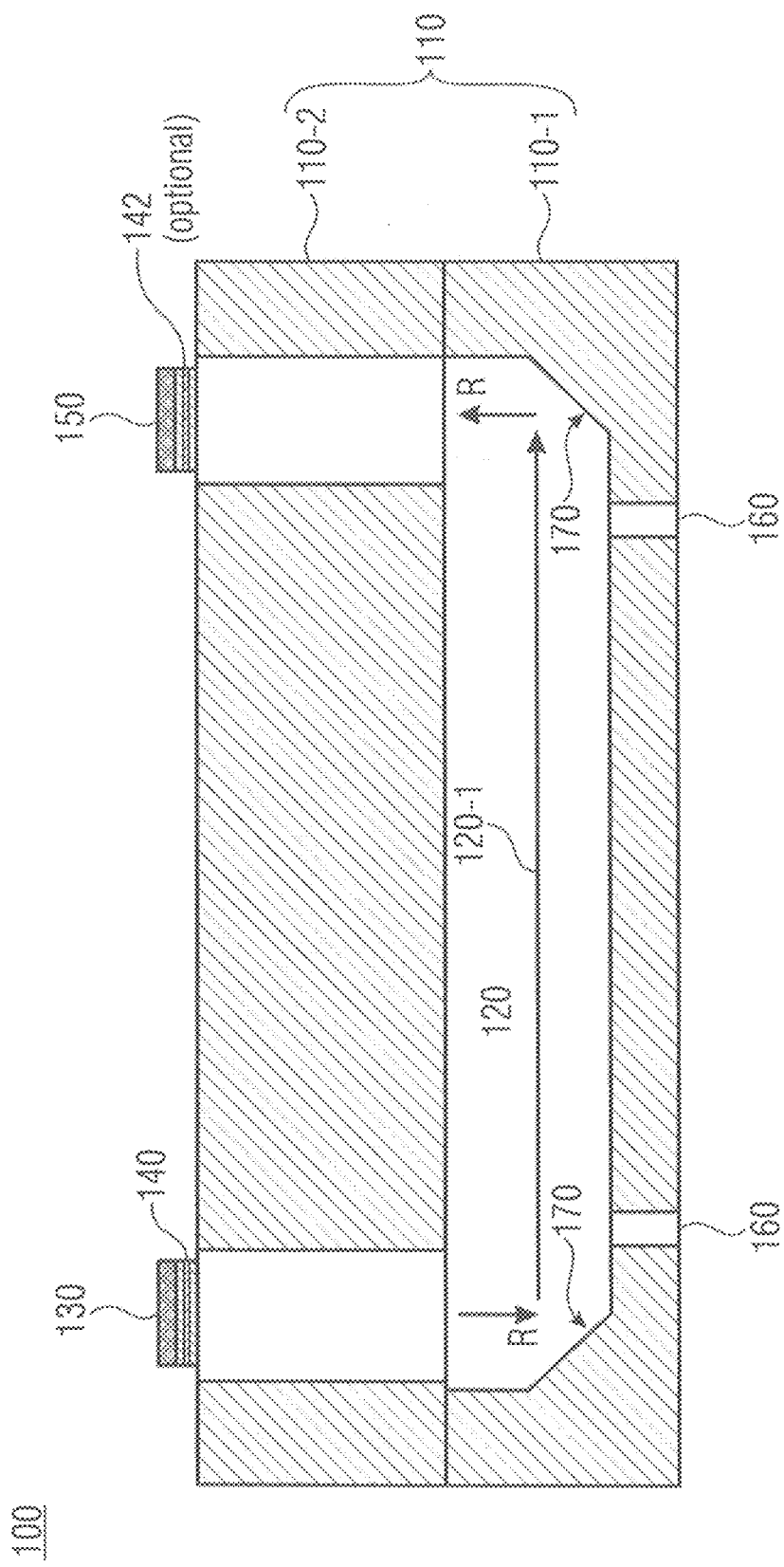

step 1
view I
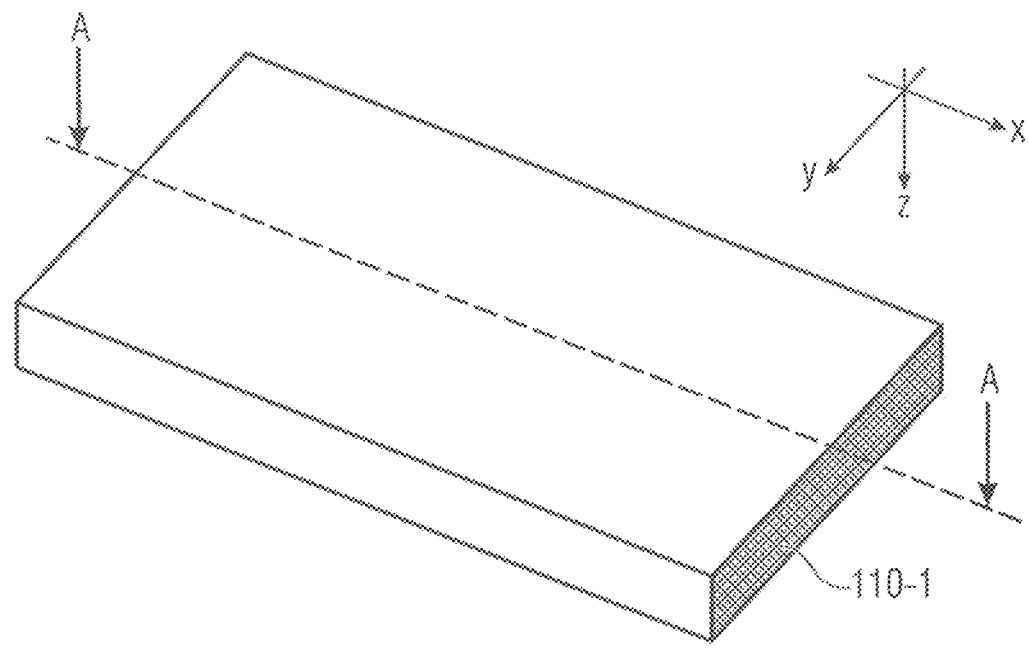
view II
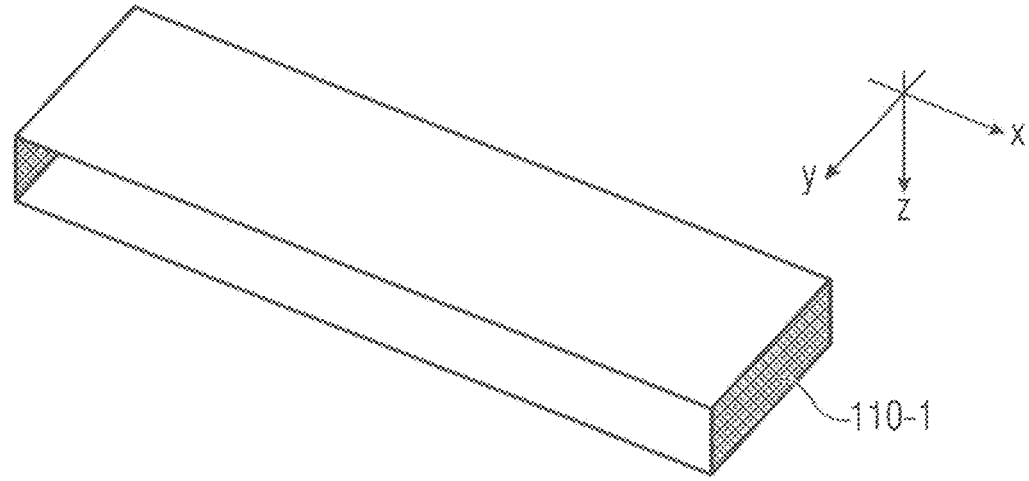
Fig. 9A step 2
view I
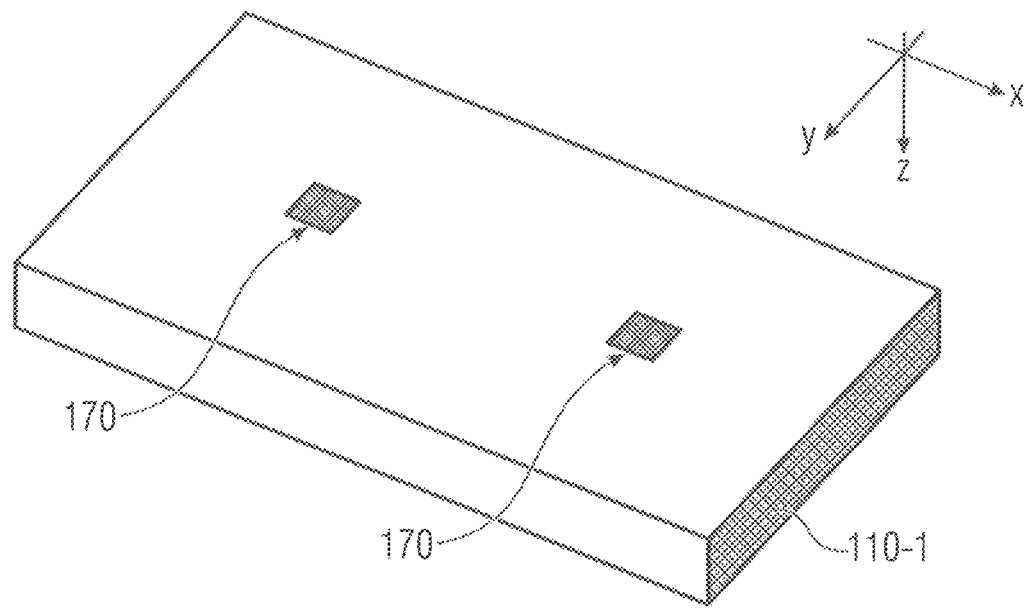
view II
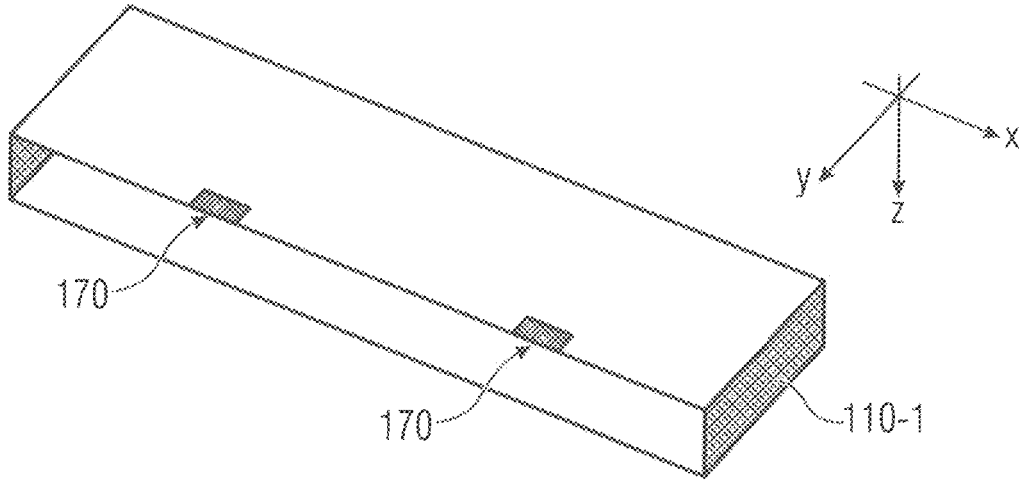
Fig. 9B step 3
view I
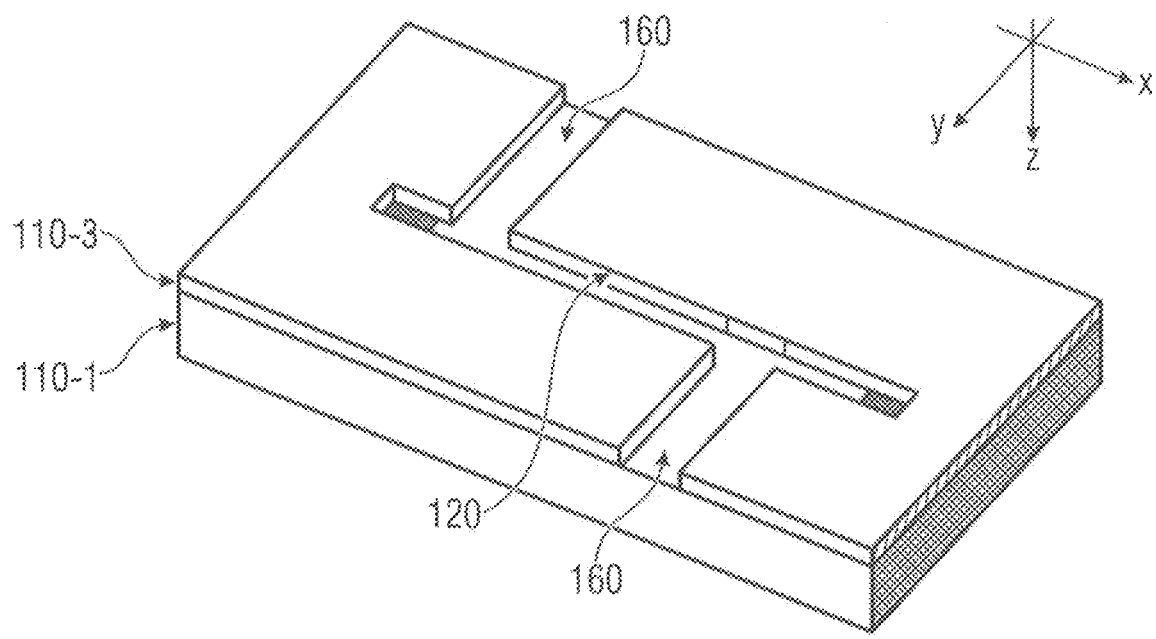
view II
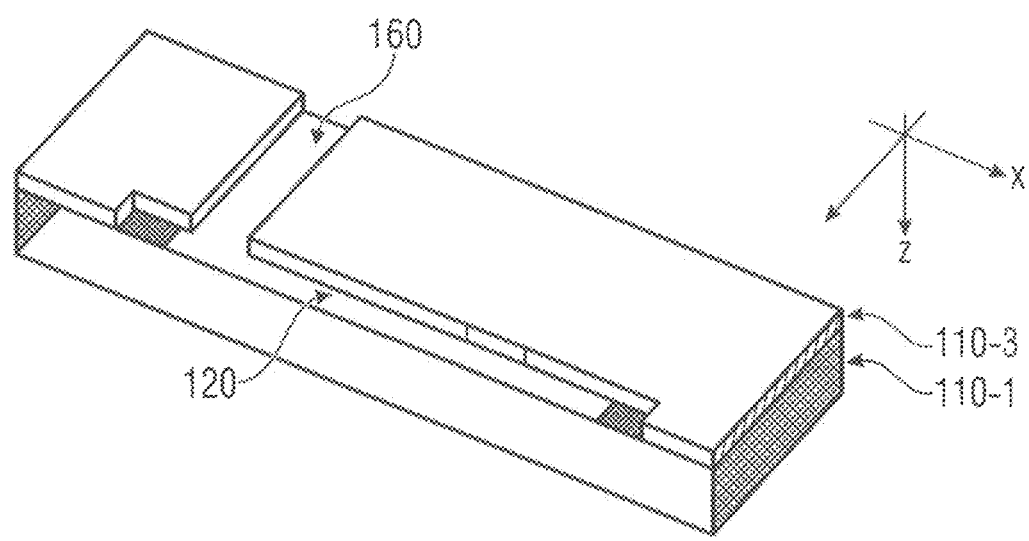
Fig. 9C step 4
view I
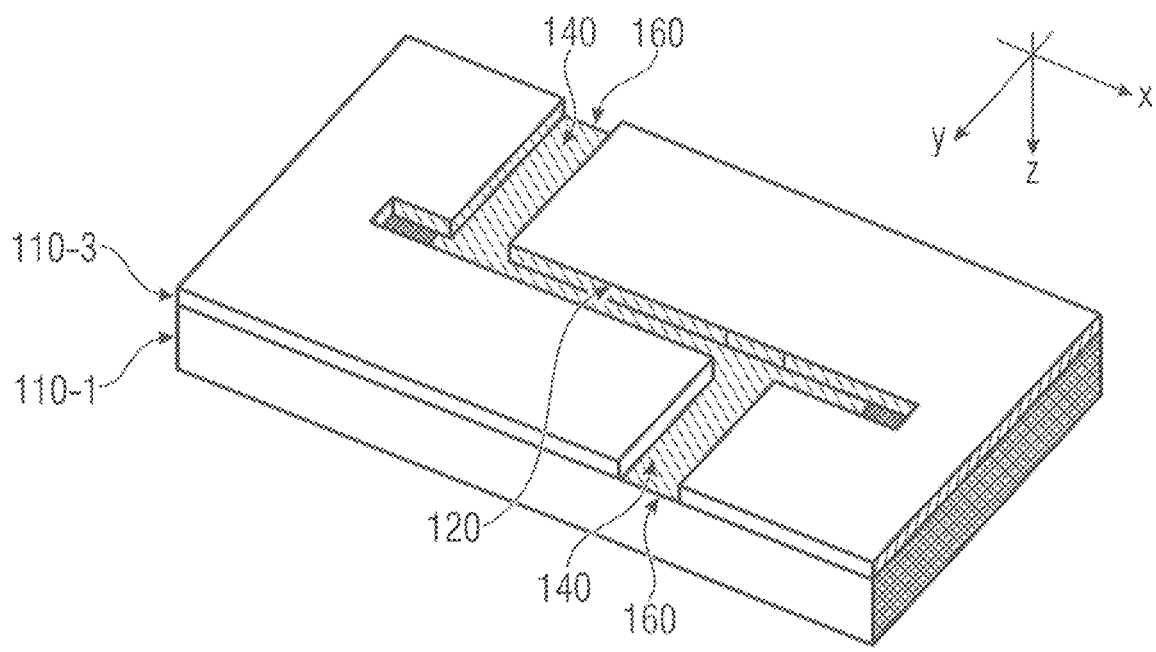
view II
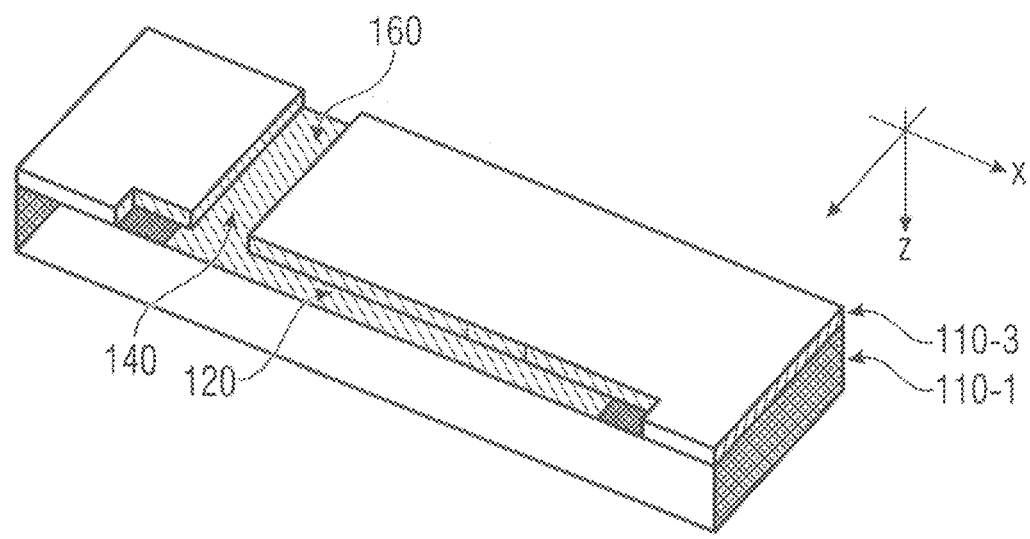
Fig. 9D step 5
view I
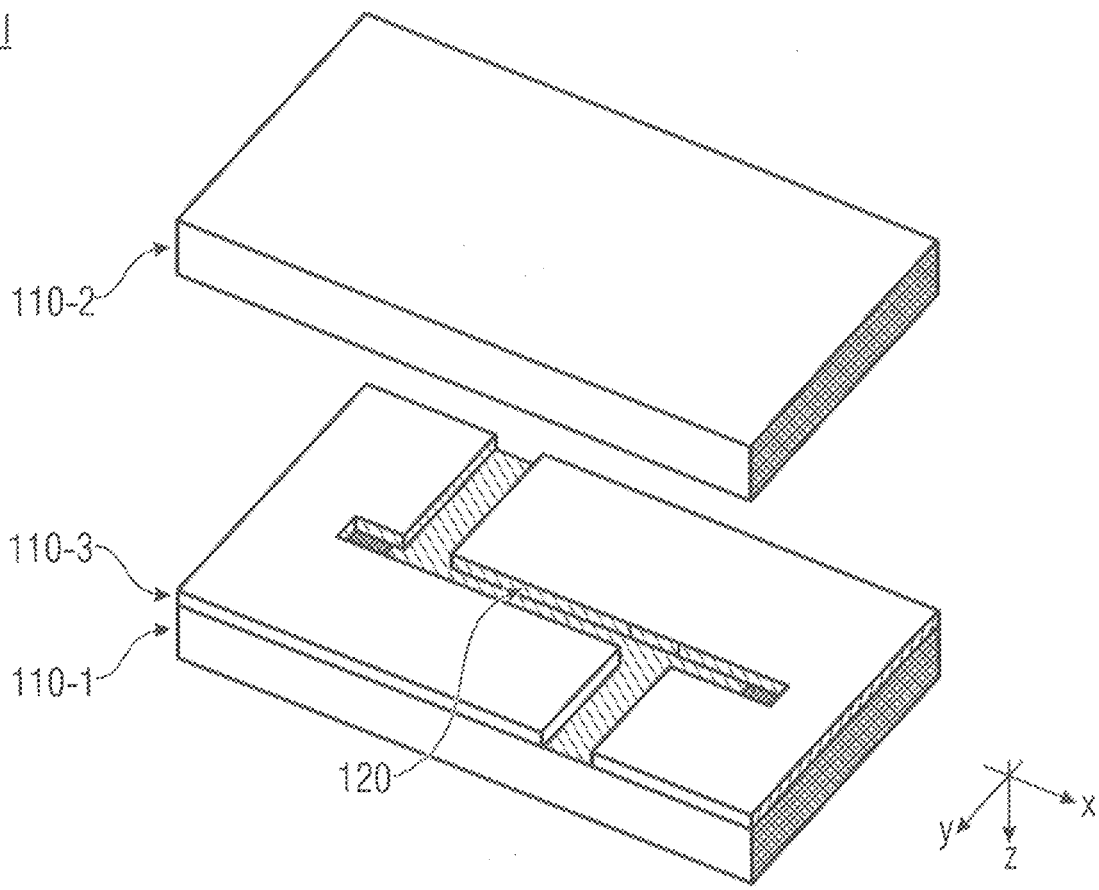
view II
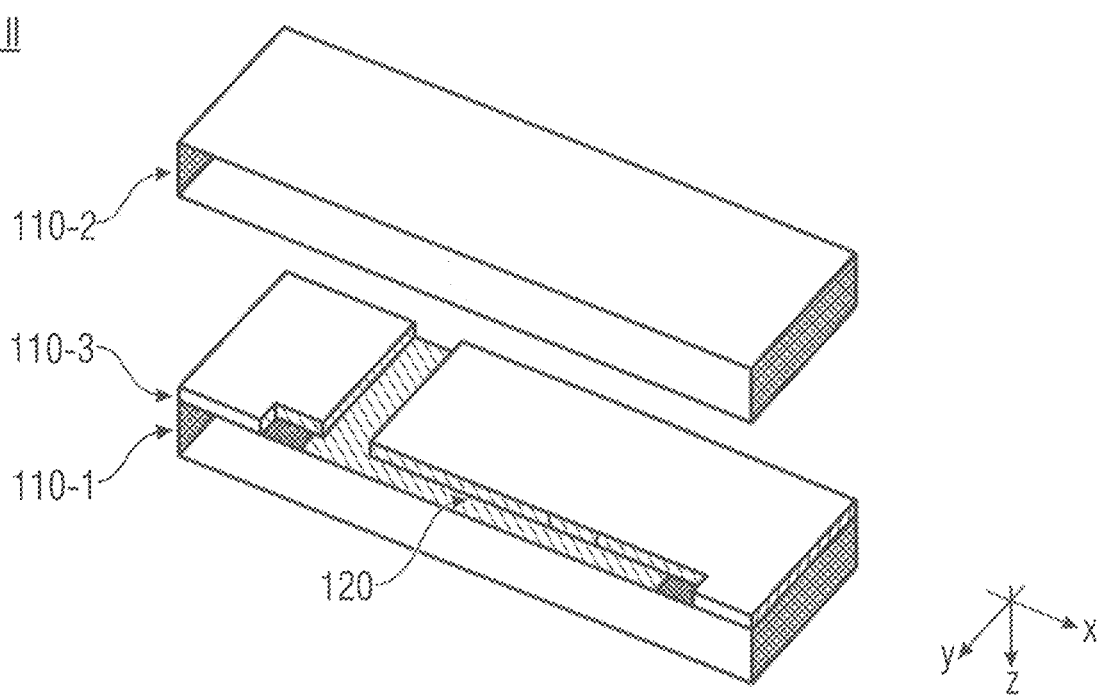
Fig. 9E step 6
view I
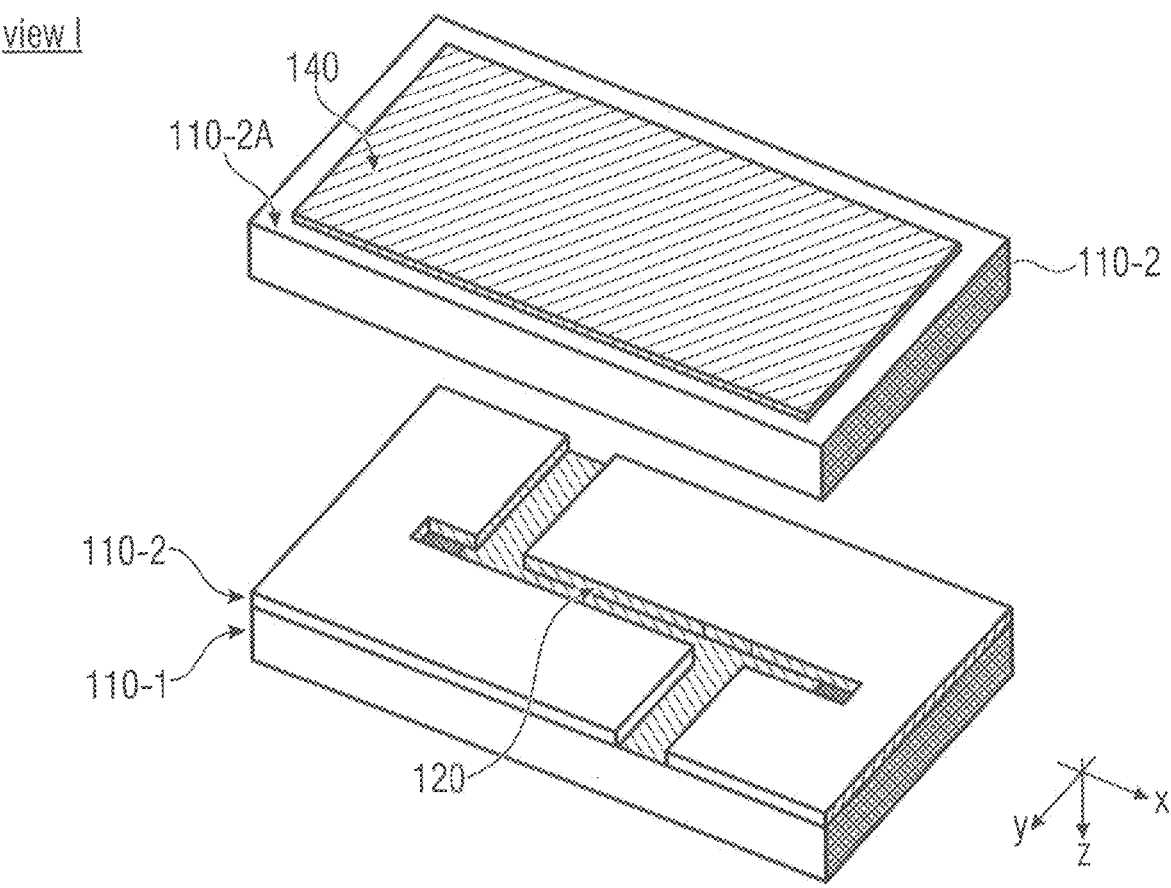
view II
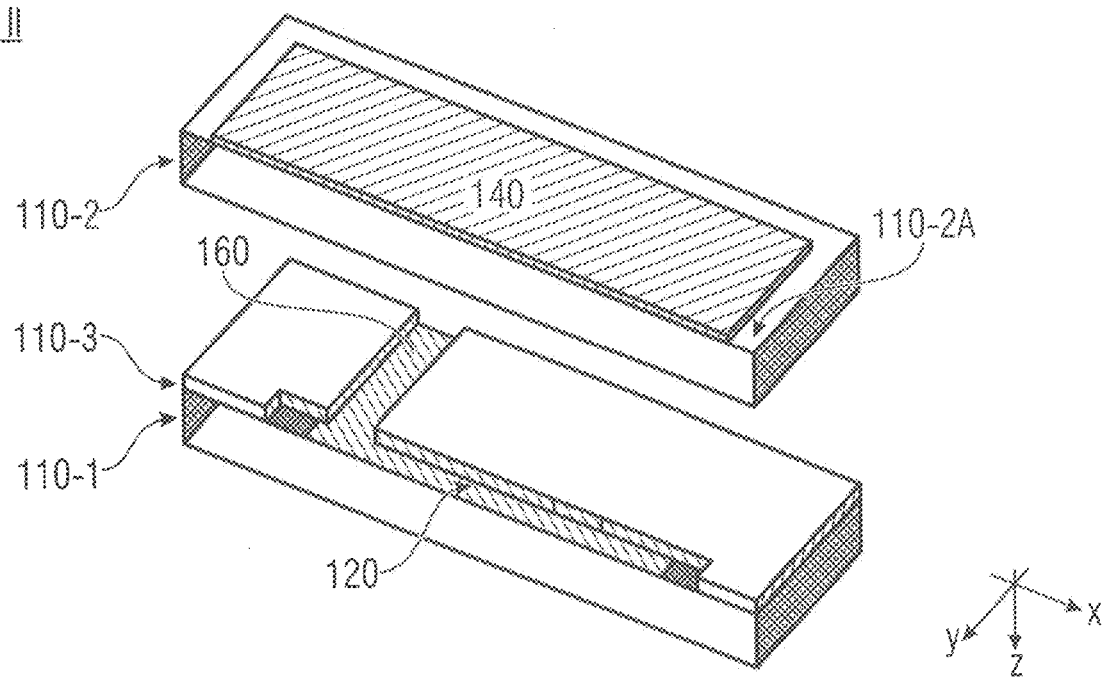
Fig. 9F step 7
view I
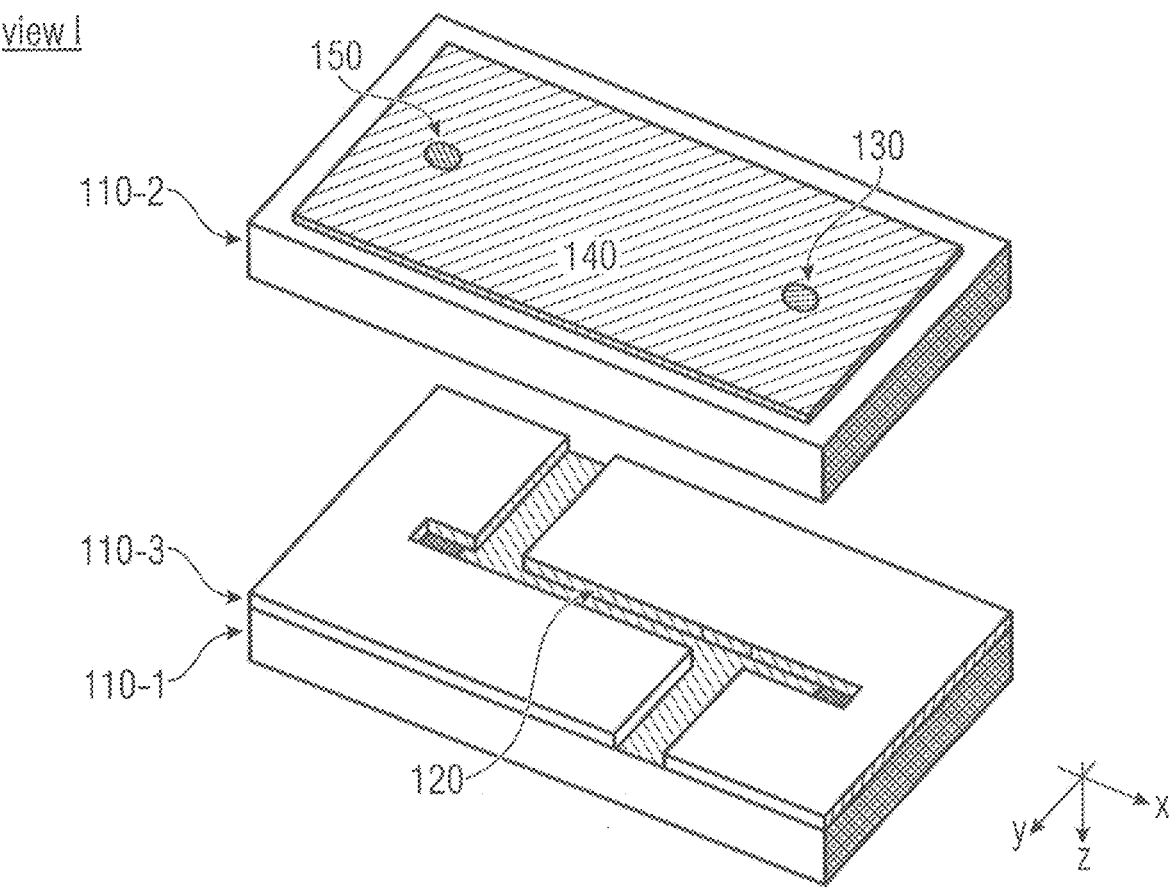
view II
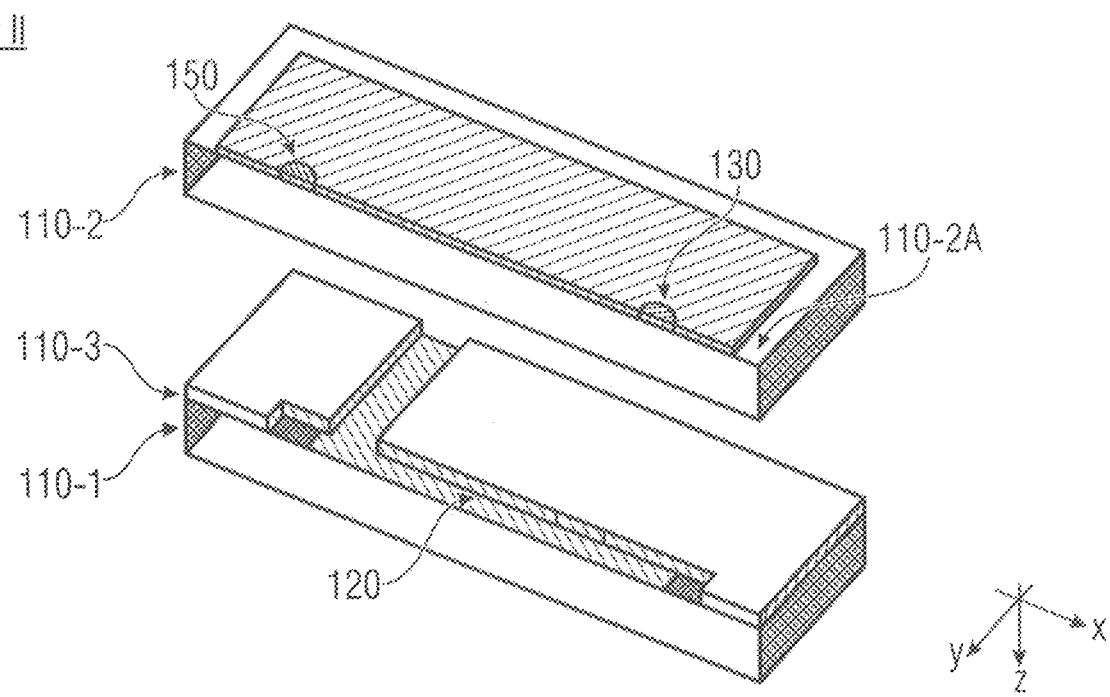
Fig. 9G

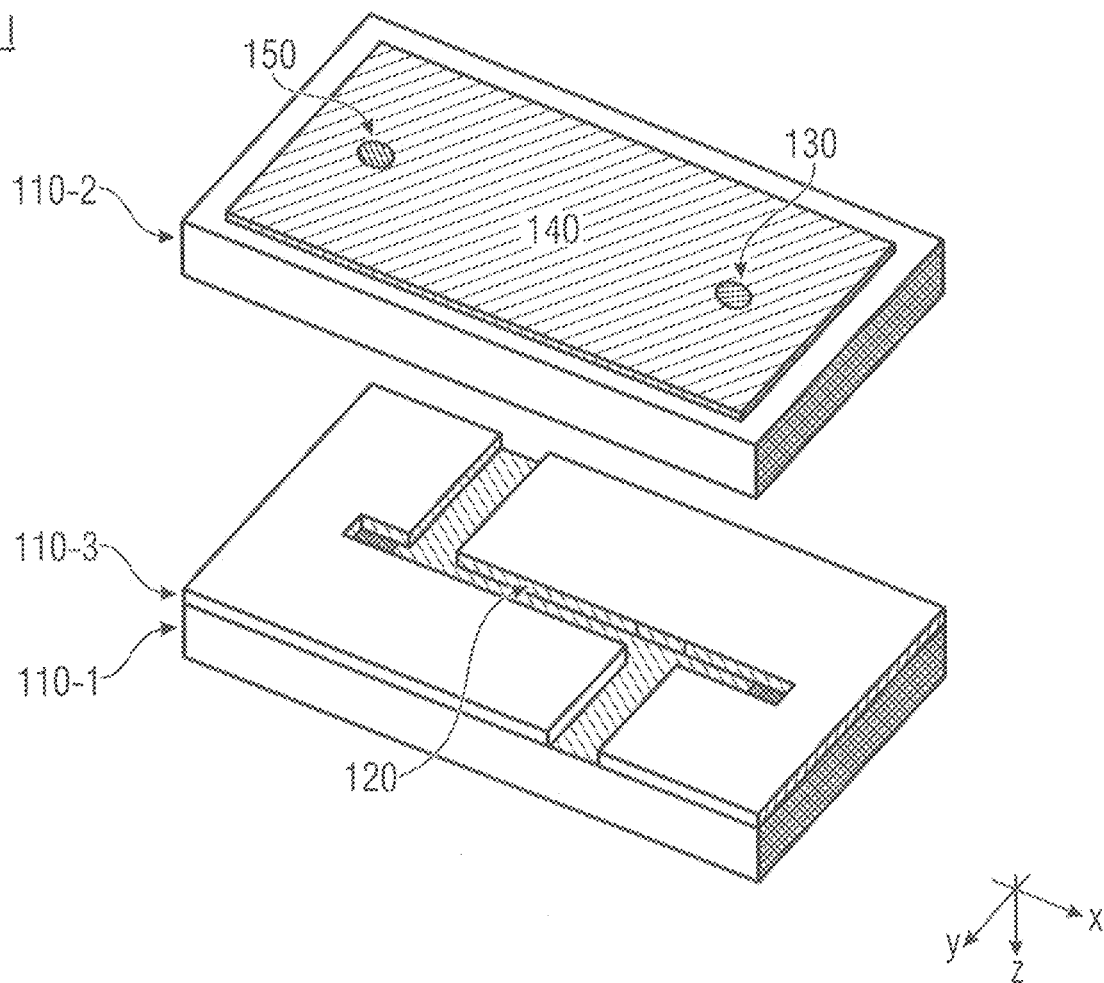
Fig. 9H (Part 1)

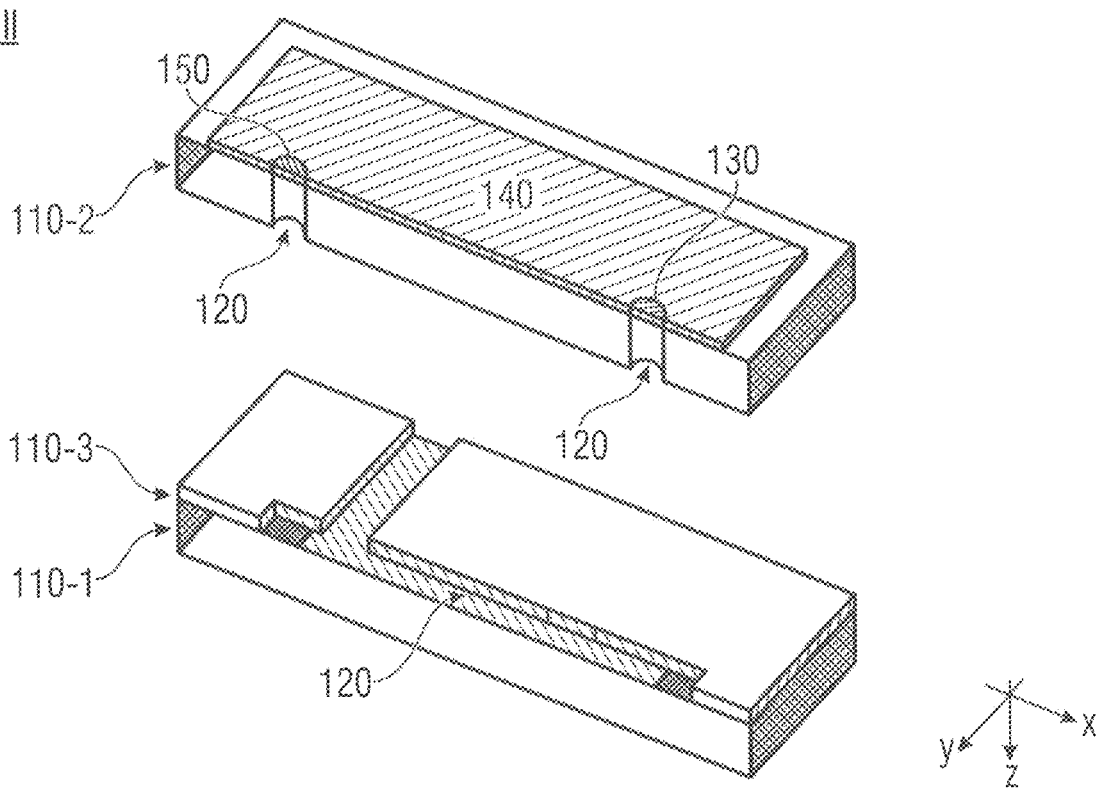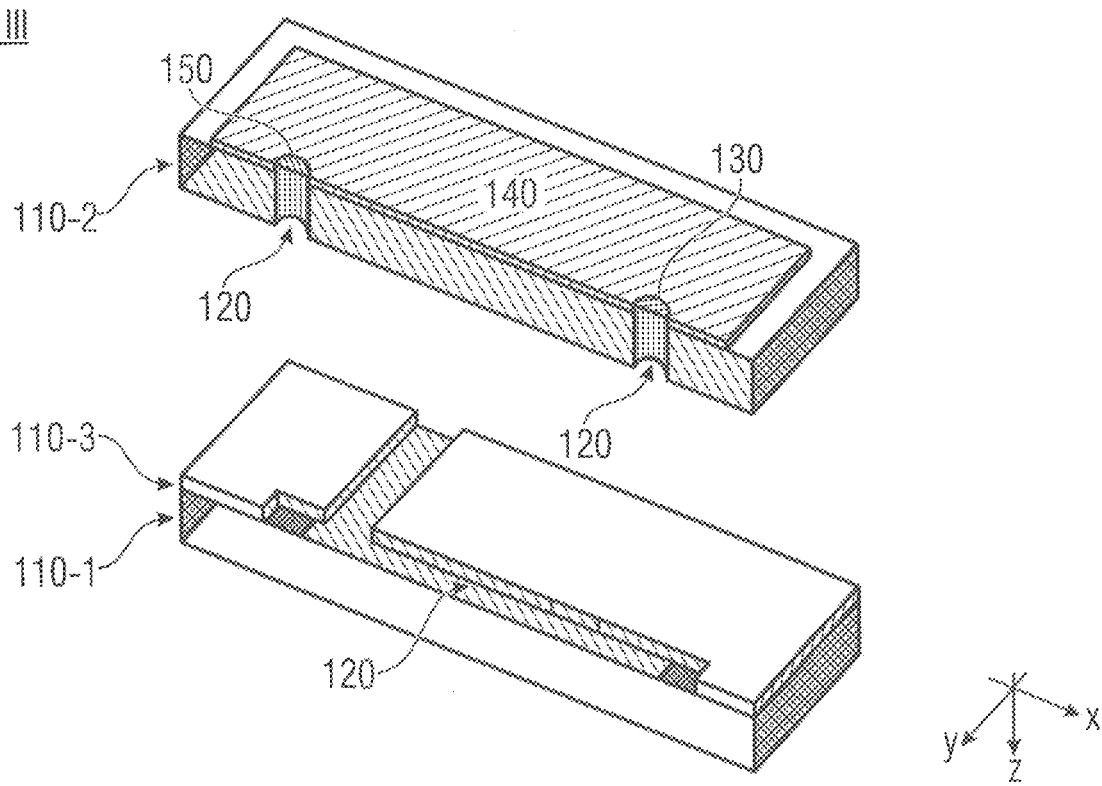
Fig. 9H (Part 2)

GAS SENSOR

This application claims the benefit of European Patent Application No. 19161699, filed on Mar. 8, 2019, which application is hereby incorporated herein by reference in its entirety.

TECHNICAL FIELD

Embodiments relate in general to the field of sensor devices and, more specifically, to the field of gas sensors.

BACKGROUND

The detection of environmental parameters in the ambient atmosphere is becoming increasingly important in the implementation of appropriate sensors within mobile devices, for example, but also in the application in home automation, such as smart home, and, for example, in the automotive sector. However, with the evermore extensive use of sensors, there is also a particular need to be able to produce such sensors as inexpensively as possible and, thus, cost effectively. However, the resulting reliability and accuracy of the sensors should nevertheless be maintained or even increased.

In particular, the field of monitoring the air quality in our environment gets more and more attention. A typical optical sensor comprises a light source, filter elements for a wavelength selection, a detector and the sample area where the light between the light source and the detector interacts with the environmental medium. Typically, such sensors are rather bulky and are assembled from discrete sub-components.

Generally, there is a need in the field for an approach to implement improved gas sensors having reduced fabrication requirements and providing an adequate sensitivity for the target gas to be detected by the sensor device.

SUMMARY

According to an embodiment, a gas sensor comprises a substrate having a cavity for providing an optical interaction path for an interaction of a filtered infrared (IR) radiation having a center wavelength $\lambda_0$ with a target gas in the cavity, wherein the cavity is accessible for an environmental gas comprising the target gas component; a thermal emitter arranged for emitting a broadband IR radiation, wherein the thermal emitter is optically coupled to the cavity; a wavelength selective structure arranged for filtering the broadband IR radiation emitted by the thermal emitter and for providing the filtered IR radiation having the center wavelength $\lambda_0$ in the cavity, wherein the wavelength selective element is optically coupled between the thermal emitter and the cavity, or wherein the wavelength selective element is formed as a bound structure of the cavity; an IR detector arranged to provide a detector output signal based on a signal strength of the filtered IR radiation having traversed the optical interaction path in the cavity and being received by the IR detector.

According to a further embodiment, a gas sensor comprises a substrate having a cavity for providing an optical interaction path for an interaction of an IR radiation component with a target gas in the cavity, wherein the cavity is accessible for an environmental gas comprising the target gas; a thermal emitter arranged for emitting a broadband IR radiation having the IR radiation component, wherein the thermal emitter is optically coupled to the cavity; an IR detector arranged to provide a detector output signal based on a signal strength of the IR radiation component having traversed the optical interaction path in the cavity and being received by the IR detector; and a wavelength selective structure arranged for filtering the broadband IR radiation emitted by the thermal emitter, wherein the wavelength selective element is optically coupled between the cavity and the IR detector for providing a filtered IR radiation comprising the IR radiation component having the center wavelength $\lambda_0$ to the IR detector.

BRIEF DESCRIPTION OF THE DRAWINGS

Embodiments of the present gas sensor are described herein making reference to the appended drawings and figures.

FIG. 2 shows a schematic cross-sectional view of an integrated gas sensor according to a further embodiment;

FIG. 4 shows a schematic cross-sectional view of an integrated gas sensor according to a further embodiment;

FIG. 5 shows a schematic cross-sectional view of an integrated gas sensor according to a further embodiment;

FIG. 8A shows a schematic cross-sectional view of an integrated gas sensor according to a further embodiment;

FIGS. 9A-9I show schematic 3D views (schematic snapshots) of the method for manufacturing an integrated gas sensor according to an embodiment.

Before discussing the present embodiments in further detail using the drawings, it is pointed out that in the figures and the specification identical elements and elements having the same functionality and/or the same technical or physical effect are usually provided with the same reference numbers or are identified with the same name, so that the description of these elements and of the functionality thereof as illustrated in the different embodiments are mutually exchangeable or may be applied to one another in the different embodiments.

DETAILED DESCRIPTION OF ILLUSTRATIVE EMBODIMENTS

In the following description, embodiments are discussed in detail, however, it should be appreciated that the embodiments provide many applicable concepts that can be embodied in a wide variety of semiconductor devices. The specific embodiments discussed are merely illustrative of specific ways to make and use the present concept, and do not limit the scope of the embodiments. In the following description of embodiments, the same or similar elements having the same function have associated therewith the same reference signs or the same name, and a description of such elements will not be repeated for every embodiment. Moreover, features of the different embodiments described hereinafter may be combined with each other, unless specifically noted otherwise.

It is understood that when an element is referred to as being "connected" or "coupled" to another element, it may be directly connected or coupled to the other element, or intermediate elements may be present. Conversely, when an element is referred to as being "directly" connected to another element, "connected" or "coupled," there are no intermediate elements. Other terms used to describe the relationship between elements should be construed in a similar fashion (e.g., "between" versus "directly between", "adjacent" versus "directly adjacent", and "on" versus "directly on", etc.).

For facilitating the description of the different embodiments, the figures comprise a Cartesian coordinate system x, y, z, wherein the x-y-plane corresponds, i.e. is parallel, to the first main surface region of the semiconductor substrate, and wherein the depth direction vertical to the first main surface region and into the semiconductor substrate corresponds to the "z" direction, i.e. is parallel to the z direction. In the following description, the term "lateral" means a direction parallel to the y-direction, wherein the term "vertical" means a direction parallel to the z-direction.

Embodiments of the present invention relate to a gas sensor. In some embodiments, the gas sensor is an integrated gas sensor, such as an integrated free-beam IR gas sensor.

Figure 1A:
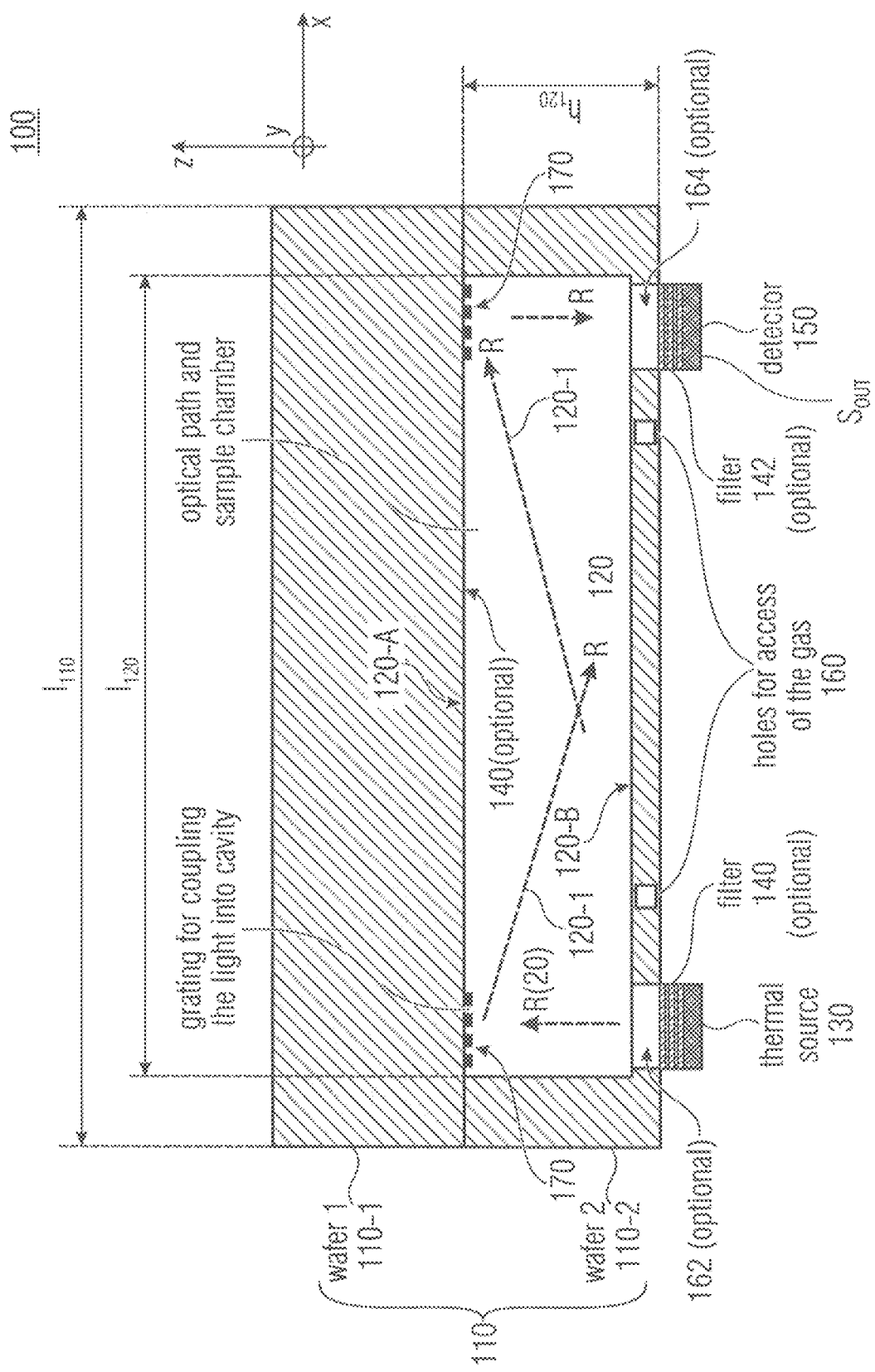
FIG. 1A shows a schematic cross-sectional view of an integrated gas sensor according to an embodiment.

FIG. 1A shows a schematic cross-sectional view of an integrated gas sensor 100 according to an embodiment for sensing an amount or a concentration of a target gas component in an environmental gas or environmental gas mixture, e.g. air. In FIG. 1A, the drawing plane is parallel to the x-z-plane.

The integrated gas sensor 100 comprises a substrate no having a cavity 120 for providing an optical interaction path 120-1 for an interaction of a filtered IR radiation "R" having a center wavelength $\lambda_0$ with a target gas in the cavity 120, wherein the cavity 120 is accessible for an environmental gas or environmental gas mixture comprising the target gas component. The integrated gas sensor 100 further comprises a thermal emitter 130 arranged for emitting a broadband or incoherent IR radiation $R_0$, wherein the thermal emitter 130 is optically coupled to the cavity 120.

The integrated gas sensor 100 further comprises a wavelength selective structure 140 arranged for filtering the broadband IR radiation $R_0$ emitted by the thermal emitter 130 and for providing the filtered (narrowband) IR radiation R having the center wavelength $\lambda_0$ in the cavity 120.

According to an embodiment, the wavelength selective element 140 may be optically coupled between the thermal emitter 130 and the cavity 120. Thus, the wavelength selective element 140 may comprise an optical band-pass filter structure, for example. According to a further embodiment, the wavelength selective element 140 may be formed as a bound structure of the cavity 120. Thus, the wavelength selective element 140 may comprise a wavelength selective coating of the cavity 120 or a photonic crystal structure laterally surrounding the cavity 120, for example. Moreover, the wavelength selective element 140 may comprise a combination of at least two of the optical band-pass filter structure between the thermal emitter 130 and the cavity 120, the wavelength selective coating of the cavity 120 and the photonic crystal structure laterally surrounding the cavity 120, for example.

The integrated gas sensor 100 further comprises an IR detector 150 which is arranged to provide a detector output signal $S_{OUT}$ based on a signal strength of the filtered IR radiation R having traversed the optical interaction path 120-1 in the cavity 120 and being received by or being incident to the IR detector 150. The IR detector 150 is sensitive for the filtered IR radiation R having the center wavelength $\lambda_0$.

The cavity 120 is arranged to provide a length $l_{120-1}$ of the optical interaction path 120-1 which is significantly, e.g. at least 100 times, larger than the center wavelength $\lambda_0$ of the filtered IR radiation R. Moreover, the part of the cavity 120 forming the optical interaction path 120-1 may be configured to guide the filtered IR radiation R having the center wavelength $\lambda_0$ by standard reflection. Standard reflection is used, in contrast to a total internal reflection, which is the mechanism in waveguides. According to an embodiment, the inner sidewall portions 120-A . . . 120-D of the cavity 120 may comprise at least partially a coating which is highly reflective for the filtered IR radiation R having the center wavelength $\lambda_0$.

In the interaction region 120-1, the target component absorbs the IR radiation R having a center wavelength $\lambda_0$, wherein the degree of absorptions depends on or is a measure of the concentration of a target gas component in an environmental gas, if the IR radiation R having a center wavelength $\lambda_0$ falls in the absorption spectrum of the target gas component.

According to an embodiment, the substrate 110 may comprise at least one access hole or opening 16o to the cavity 120 for providing an access and/or exchange of the environmental gas having the target gas component to the cavity 120. The at least one access hole 160 may comprise a plurality of access holes 160 or may form a perforation in the substrate 110.

As shown in FIG. 1A, the optical interaction path 120-1 may extend parallel or essentially parallel to a bottom sidewall (first main surface region) 120-A and a top sidewall (second main surface region) 120-B of the cavity 120 so that the filtered IR radiation R is guided along or essentially along a lateral plane (parallel to the x-y-plane of FIG. 1A) of the substrate 110.

According to an embodiment, the bottom sidewall 120-A and the top sidewall 120-B of the cavity 120 may extend along the optical interaction path 120-1 parallel to each other for providing an essentially constant height $h_{120}$ of the cavity 120 along the optical interaction path 120. The height $h_{120}$ of the cavity 120 may be larger than the center wavelength $\lambda_0$, with $h_{120>\lambda 0}$, with $h_{120}$ about 10 to 100 µm. The length $l_{120}$ of the cavity 120 which defines the interaction length in the gas may be adopted to the absorption by the gas and may correspond to an effective length of 1-5 mm in the case of $CO_2$ (for the 4.26 µm absorption band). The width $w_{120}$ (parallel to the y-direction in FIG. 1A) of the cavity 120 can be similar to its height $h_{120}$ (or significantly larger and more complex, including areas with focusing and refocusing structures 170 in the case of 2D-optics). Finally, the layers within the filter structure(s) 140 may be on the order of 0.15-2 µm, for example.

According to embodiments, the filtered IR radiation R propagates along the optical interaction path 120-1 in the cavity 120 with the center wavelength $\lambda_0$, if the medium or gas in the cavity 120 may be considered to have a refractive index n=1 (or n≈1). In case, the medium or gas in the cavity 120 has a refractive index n≠1, the filtered IR radiation R has the resulting center wavelength $\lambda_0/n$.

According to an embodiment, the cavity 120 of the gas sensor 100 may comprise at least partially, e.g. except for coupling regions (see FIG. 7A, for example), along the optical interaction path 120-1 vertical (e.g., parallel to the x-z- and/or y-z-plane of FIG. 1A) sidewalls 120-C, 120-D.

According to an embodiment, the cavity 120 of the gas sensor 100 may comprise in a cut view parallel to the x-y-plane of FIG. 1A a meander shape or a spiral shape for providing an accordingly shaped optical interaction path 120-1 and for providing a resulting length $l_{120-1}$ of the optical interaction path 120-1 which is larger than the lateral dimension $l_{110}$ of the substrate no. The length $l_{120-1}$ of the optical interaction path 120-1 may be at least 2, 5 or 10 times larger than the lateral dimension $l_{110}$ of the substrate no.

As shown in FIG. 1A, the substrate no may comprise a first partial substrate (first wafer) 110-1 and a second partial substrate (second wafer) 110-2 which are bonded to each other. At least one of the first and second partial substrates 110-1, 110-2 comprises a recess for providing the cavity 120 between the first and second bonded partial substrates 110-1, 110-2. At least one of the first and second partial substrates 110-1, 110-2 comprises a further recess 120 for providing the at least one access hole 160 to the cavity 120. Thus, the first partial substrate 110-1 may form the cover of the cavity 120 for providing the optically closed cavity 120 along the optical interaction path 120-1 for the propagating filtered IR radiation R having the center wavelength $\lambda_0$.

As shown in FIG. 1A, the gas sensor 100 may further comprise at least one radiation directing element 170, e.g. a mirror and/or grating, in the cavity 120 for directing or coupling the filtered IR radiation R into the optical interaction path 120-1 and/or for focusing the filtered IR radiation R to the IR detector 150, e.g. on the radiation detecting/sensitive surface of the IR detector 150.

According to an embodiment, the IR emitter 130 may comprise a conductor, e.g. a semiconductor strip and/or metallic strip, having a main emission surface region for emitting a broadband IR radiation $R_0$ in a main radiation emission direction, which is vertical (normal) to the plane of the main emission surface region, for example. The conductor may comprise a highly-doped semiconductor strip, wherein a metallic cover layer at least partially covers the main emission surface region of the semiconductor strip. Thus, the semiconductor strip may comprise a highly doped silicon material to form a black body radiator and may be configured to have in an actuated condition an operating temperature in a range between 600 and 1000 K. The IR emitter 130 may be connected to a power source (not shown in FIG. 1A) for providing the electrical energy as actuation signal to bring the IR emitter 130 in the actuated condition for radiation emission.

In case, the main radiation emission direction of the IR emitter 130 is angularly offset to a lateral extension plane (e.g., the x-y-plane of FIG. 1A) of the cavity 120, the gas sensor 100 may comprise the radiation directing element(s) 170 in form of a deflection structure in the cavity 120 for deflecting or directing the filtered IR radiation R into the optical interaction path 120-1 of the cavity 120. As shown in FIG. 1A, the main radiation emission direction of the IR emitter 130 may be perpendicular to a lateral extension plane of the cavity 120 and, thus, (essentially) perpendicular to the optical interaction path 120-1 of the filtered IR radiation R in the cavity 120.

According to an embodiment, the wavelength selective structure 140 may be formed as an optical band-pass filter structure having a narrow transmission band for providing the filtered IR radiation R having the center wavelength $\lambda_0$. According to an embodiment, the wavelength selective structure 140 may comprise at least one of a filter structure between the IR emitter 130 and the cavity 120, a photonic crystal structure in lateral sidewall regions 120-C, 120-D of the cavity 120, and a wavelength selective coating of inner wall regions 120-A . . . 120-D of the cavity 120 for providing the filtered (narrowband) IR radiation R having the center wavelength $\lambda_0$ in the cavity 120.

As shown in FIG. 1A, a region 162 of the substrate 110, in which the radiation R transmits to enter the cavity 120 and on which the emitter 130 is located, and the region 164 of the substrate 110, in which the radiation R transmits to exit the cavity 120 and on which the detector 150 is located, may be formed as openings. If the substrate material of the regions 162, 164, on which the emitter 130 and detector 150 are located, is sufficiently optically transparent, it is not necessary for the openings 162, 164 to be provided through the substrate material to the cavity 120 at the emitter 130 and the detector 150.

According to a further embodiment, a further wavelength selective structure 142 may be optionally arranged for further filtering the IR radiation R propagated through the optical interaction path 120-1 and directed to the IR detector 150. The further wavelength selective element 142 may be optically coupled between the cavity 120 and the IR detector 150 for providing a further filtered, narrowband IR radiation R having the center wavelength $\lambda_0$ to the IR detector. The further wavelength selective element 142 may comprise an optical band-pass filter structure, for example.

According to an embodiment, the IR detector 150 may comprise a resistive temperature sensor, a pyroelectric temperature sensor, a piezoelectric temperature sensor or a pn junction temperature sensor, which is configured to provide the detector output signal $S_{OUT}$ based on a signal strength of the filtered IR radiation R propagated through the optical interaction path 120-1 of the cavity 120 and is incident on the IR detector 150 and, thus, is sensed by IR detector 150. Thus, the IR detector 150 may be configured to sense the strength of the incident filtered IR radiation R. Due to the interaction of the filtered IR radiation R with the target gas component in the cavity 120, the strength of the incident filtered IR radiation R is a measure of the concentration of the target gas in the cavity 120. Thus, the concentration of the target gas in the surrounding atmosphere of the gas sensor is derivable from the output signal $S_{OUT}$ of the IR detector iso.

Figure 1B:
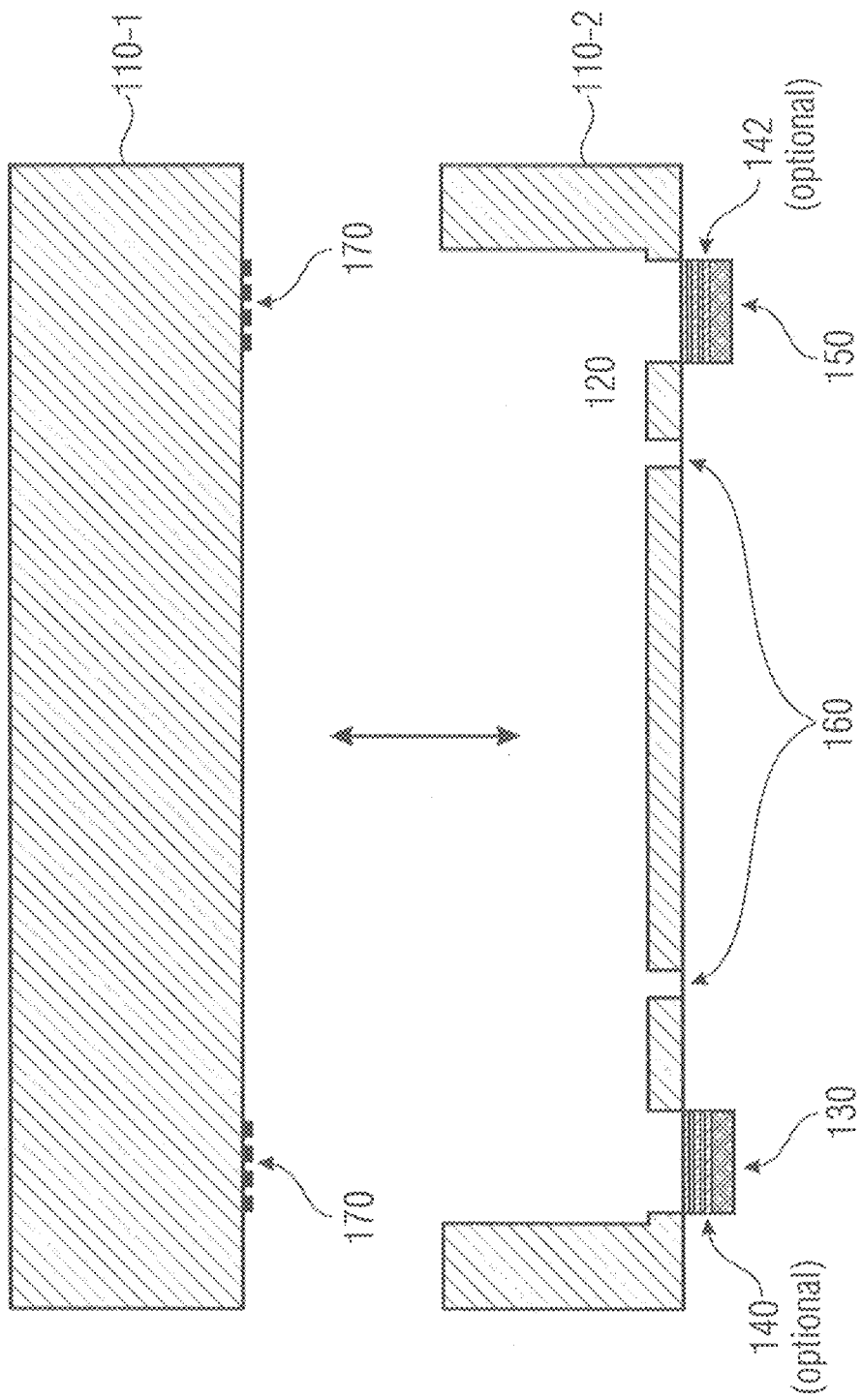
FIG. 1B shows a schematic cross-sectional view of a top wafer and a bottom wafer in a separated condition, e.g., before bonding the two wafers.

FIG. 1B shows a schematic cross-sectional view of a first partial substrate (top wafer) 110-1 and a second partial substrate (bottom wafer) 110-2 in a separated condition, e.g., before bonding the two partial substrates to achieve the bonded substrate no. At least one of the first and second partial substrates 110-1, 110-2 may comprise a recess for providing the cavity 120 between the first and second bonded partial substrates 110-1, 110-2. At least one of the first and second partial substrates 110-1, 110-2 comprises a further recess 120 for providing the at least one access hole 160 to the cavity 120. Thus, the first partial substrate 110-1 may form the cover of the cavity 120 for providing the optically closed cavity 120 along the optical interaction path 120-1 for the propagating filtered IR radiation R having the center wavelength $\lambda_0$.

Thus, the cavity 120 may be realized via wafer bonding technology. In this case, the second partial substrate (bottom wafer) 110-2 may comprise the cavity, which may be generated e.g., by means of a Bosch-etching process), and the source or emitter structures 130 and the detector structures iso. The first partial substrate (top wafer) 110-1 is arranged vertically on top of the second partial substrate (bottom wafer) 110-2. The first partial substrate (top wafer) 110-1 may comprise the grating structures 170 for light deflection, e.g. realized as 50 nm (or between 30 and 70 nm) high lines of poly-silicon with a 2 µm (or a 1 to 3 µm) pitch, for example. According to an embodiment, first partial substrate (top wafer) 110-1 may also comprise a glass wafer in order to use anodic bonding with the second partial substrate (bottom wafer) 110-2. In this case, the temperature exposure during the bonding process has to be considered in order to avoid a damage of the metallized areas. The region or inner wall(s) of the cavity 120 may be metallized, e.g. with Au, to ensure reflectivity.

In the present description of embodiments, the same or similar elements having the same structure and/or function are provided with the same reference numbers or the same name, wherein a detailed description of such elements will not be repeated for every embodiment. Thus, the above description with respect to FIGS. 1A-1B is equally applicable to the further embodiments as described below. In the following description, essentially the differences, e.g. additional elements, to the embodiment as shown in FIGS. 1A-1B and the technical effect(s) resulting therefrom are discussed in detail.

FIG. 2 shows a schematic cross-sectional view of an integrated gas sensor 100' according to a further embodiment.

As shown in FIG. 2, the integrated gas sensor 100' comprises a substrate no having a cavity 120 for providing an optical interaction path 120-1 for an interaction of an IR radiation component with a target gas in the cavity 120, wherein the cavity 120 is accessible for an environmental gas or environmental gas mixture comprising the target gas component.

The integrated gas sensor 100 further comprises a thermal emitter 130 arranged for emitting a broadband or incoherent IR radiation $R_0$ having the IR radiation component R, wherein the thermal emitter 130 is optically coupled to the cavity 120.

The integrated gas sensor boo further comprises an IR detector 150 arranged to provide a detector output signal $S_{OUT}$ based on a signal strength of the IR radiation component R having traversed, e.g. as part of the broadband IR radiation $R_0$, the optical interaction path 120-1 in the cavity 120 and being received by or being incident to the IR detector 150. The IR detector 150 is sensitive for the IR radiation component R having the center wavelength $\lambda_0$.

The integrated gas sensor 100 further comprises a wavelength selective structure 142 arranged for filtering the broadband IR radiation $R_0$ emitted by the thermal emitter 130, wherein the wavelength selective element 142 is optically coupled between the cavity 120 and the IR detector 150 for providing a filtered, narrowband IR radiation R comprising the IR radiation component having the center wavelength $\lambda_0$ to the IR detector 150. The wavelength selective element 142 may comprise an optical band-pass filter structure, for example.

According to an embodiment, the integrated gas sensor 100 may further comprise a further IR detector 152 arranged to provide a further detector output signal $S'_{OUT}$ based on a signal strength of the further IR radiation component R' having traversed, e.g. as part of the broadband IR radiation $R_0$, the optical interaction path 120-1 in the cavity 120 and being received by or being incident to the IR detector. The further IR detector 152 is sensitive for the further IR radiation component R' having the further center wavelength $\lambda_1$.

According to an embodiment, a further wavelength selective structure 144 arranged for filtering the broadband IR radiation $R_0$ emitted by the thermal emitter 13o, wherein the further wavelength selective element 144 is optically coupled between the cavity 120 and the further IR detector 152 for providing a further filtered, narrowband IR radiation R' comprising the further IR radiation component R' having the further center wavelength $\lambda_1$ to the further IR detector 152. The further wavelength selective element 142 may comprise an optical band-pass filter structure, for example.

The above description with respect to the structure and functionality of the IR detector 150 and the wavelength selective structure 140 is equally applicable to the further IR detector 152 and the further wavelength selective structure 142.

When comparing the embodiments the integrated gas sensor 100 as shown in FIG. 1A and the integrated gas sensor 100' as shown in FIG. 2, the integrated gas sensor 100 according to FIG. 1A uses the wavelength selective structure 140 to filter the broadband IR radiation $R_0$ emitted by the IR emitter 130 and to provide a filtered IR radiation R having a center wavelength $\lambda_0$, which propagates along the optical interaction path 120-1 in the cavity 120.

The integrated gas sensor 100' as shown in FIG. 2 may use a broadband IR radiation $R_0$ which propagates along the optical interaction path 120-1 in the cavity 120. The broadband IR radiation $R_0$ may comprise the IR radiation component R having the center wavelength $\lambda_0$ for interacting with the target gas component. The broadband IR radiation $R_0$ may further comprise the further IR radiation component R' having the center wavelength $\lambda_1$ for interacting with a further target gas component. The wavelength selective structure 142 is arranged to filter the broadband IR radiation $R_0$ when leaving the cavity 120 and before reaching the IR detector 150 so that the IR detector 150 receives the IR radiation component R having the center wavelength $\lambda_0$. In the optional case of a two detector arrangement, the further wavelength selective structure 144 is arranged to filter the broadband IR radiation $R_0$ when leaving the cavity 120 and before reaching the further IR detector 152 so that the further IR detector 152 receives the further IR radiation component R' having the center wavelength $\lambda_1$.

The integrated gas sensor 100' as shown in FIG. 2 may comprise multiple detectors 150, 152, which are sensitive to different wavelengths $\lambda_0$, $\lambda_1$, for example. Each detector 150, 152 of the plurality of detectors may comprise a dedicated narrow-band filter 140, 142. Providing multiple detectors 150, 152 may provide a reference signal at a $2^{nd}$ wavelength $\lambda_1$ and may also potentially be used for multi-gas sensing by detection characteristic lines of several target gases in parallel. This concept is further applicable to more than two detectors.

Thus, the above description with respect to the further elements and structures of the integrated gas sensor 100 of FIGS. 1A-1B is equally applicable to the integrated gas sensor 100' of FIG. 2. Please note that the drawings are not to scale. In fact, the cavity length $l_{120}$ may be much larger compared to its height $h_{120}$, in order to ensure significant interaction lengths.

The properties of the integrated gas sensor 100, 100' can be summarized as follows.

The integrated gas sensor 100, 100' can be used in consumer electronics, for example, as it can be realized with semiconductor technology with relatively low efforts. The present concept proposes a scheme to combine all parts of the integrated gas sensor 100, 100' in a single integrated design, which is realizable with semiconductor technologies, wherein fully functional optical gas sensors can be implemented within a single chip. The integrated (optical) gas sensor 100, 100' provides a high selectivity, a high accuracy and fast response times. The realization of the integrated gas sensor 100, 100' in form of a chip-scale mass-producible sensor system (System-on-Chip) can be the basis for numerous applications in consumer devices. The integrated gas sensor 100, 100' further provides for a CMOS compatible miniaturized infrared (IR) absorption gas sensor, wherein optical IR spectroscopy provides to potential of high selectivity and fast response times for reliably monitoring the air quality in our environment. Also integration in large sensor networks or dense environmental monitoring may be possible applications. Increased reliability of optical sensors is an important asset in automotive applications, e.g. for monitoring of $CO_2$ levels.

According to the present concept, an optical gas sensor 100, 100' which comprises an IR source 130, filter elements 140, 142, 144, an IR detector 150, 152, and an interaction path 120-1 realized as a cavity 120 in the silicon 110, wherein the sample chamber 120 and the optical path 120-1 are realized as an integrated cavity 120, where light, e.g. IR radiation, is guided in the plane of the wafer no. This cavities 120 can for example be generated via wafer-bonding processes and can be arbitrarily shaped in order to provide the sample chamber 120 in an integrated miniaturized IR-absorption gas sensor 100, 100'. In a form, this cavity 120 can feature a linear interaction path 120-1 but more generally a "2D optical bench" may be realized, including focusing or even dispersive optical elements 170. Based on the herein described designs, reasonable path-lengths $l_{120}$ for optical absorption (interaction of the IR radiation and the target gas) are achievable. Also the relatively large cavity cross-sections (compared to single mode waveguides, for example) will increase the throughput and facilitate the use of thermal emitters 130 as radiation sources, which are easy to fabricate. All elements of an optical sensor 100, 100' are included and can be fabricated based on Si-based semiconductor technology.

A possible realization of the integrated gas sensor 100, 100' provides a long cavity 120, where the light R passes and where gas can enter and interact with the radiation R. A thermal IR source 130 together with a filter structure 140, 142, 144 generates the radiation R, which is detected at the other end of the cavity 120 with a suitable detector 150, 152. The inside of the cavity 120 is reflective, for example. The light is coupled into the cavity 120, which can be achieved with a grating 170.

In order to realize a complete integrated gas sensor 100, 100', the light R from the source 130 is coupled-in efficiently and, after the interaction with the target gas, is guided to the detector iso. A typical realization may make use of a thermal emitter 130 with a filter element 14o, 142, e.g. in front of the detector 150 or in front of the emitter 130 or both. The emitter 130 and the filter 140, which typically is based on complex thin layer structures, e.g. filter structures, are fabricated so that it emits the light R in a direction perpendicular to the cavity 120, for example. The present description shows different solutions to bend the beam, e.g. based on grating structures which may be achieved with an anisotropic etching process.

The present concept of the integrated gas sensor 100, 100' works as an infrared absorption sensor. As a consequence it provides a high selectivity, accuracy and fast response times.

Furthermore it is a basically contact-less measurement method. Moreover, the integrated gas sensor 100, 100' enables the integration into a single integrated system, which is producible via semiconductor technologies. Thus the resulting sensor 100, 100' can be realized very small and is mass producible by using a free beam approach. Thus the proposed concept uses the full field for the interaction with the medium and, in addition, the cross section of the cavities 120 is much larger compared to single mode waveguides (where the cross section must be on the order of the wavelength). This will enable higher optical throughput and higher sensitivity and will enable shorter interaction path-lengths. Furthermore there will be lower damping than in the waveguides.

The integrated gas sensor 100, 100' provides a fully integrated nondispersive infrared (NDIR) micro gas sensor which can be produced based on standard Si semiconductor technology and which has a cavity 120, which is larger than the wavelength of the light and which the (target) gas can penetrate. This allows the realization of an integrated NDIR sensor in chip-scale.

In the following, a number of different possible implementations of the integrated gas sensor 100, 100' are exemplarily described. In the present description of embodiments, the same or similar elements having the same structure and/or function are provided with the same reference numbers or the same name, wherein a detailed description of such elements will not be repeated for every embodiment.

Figure 3A:
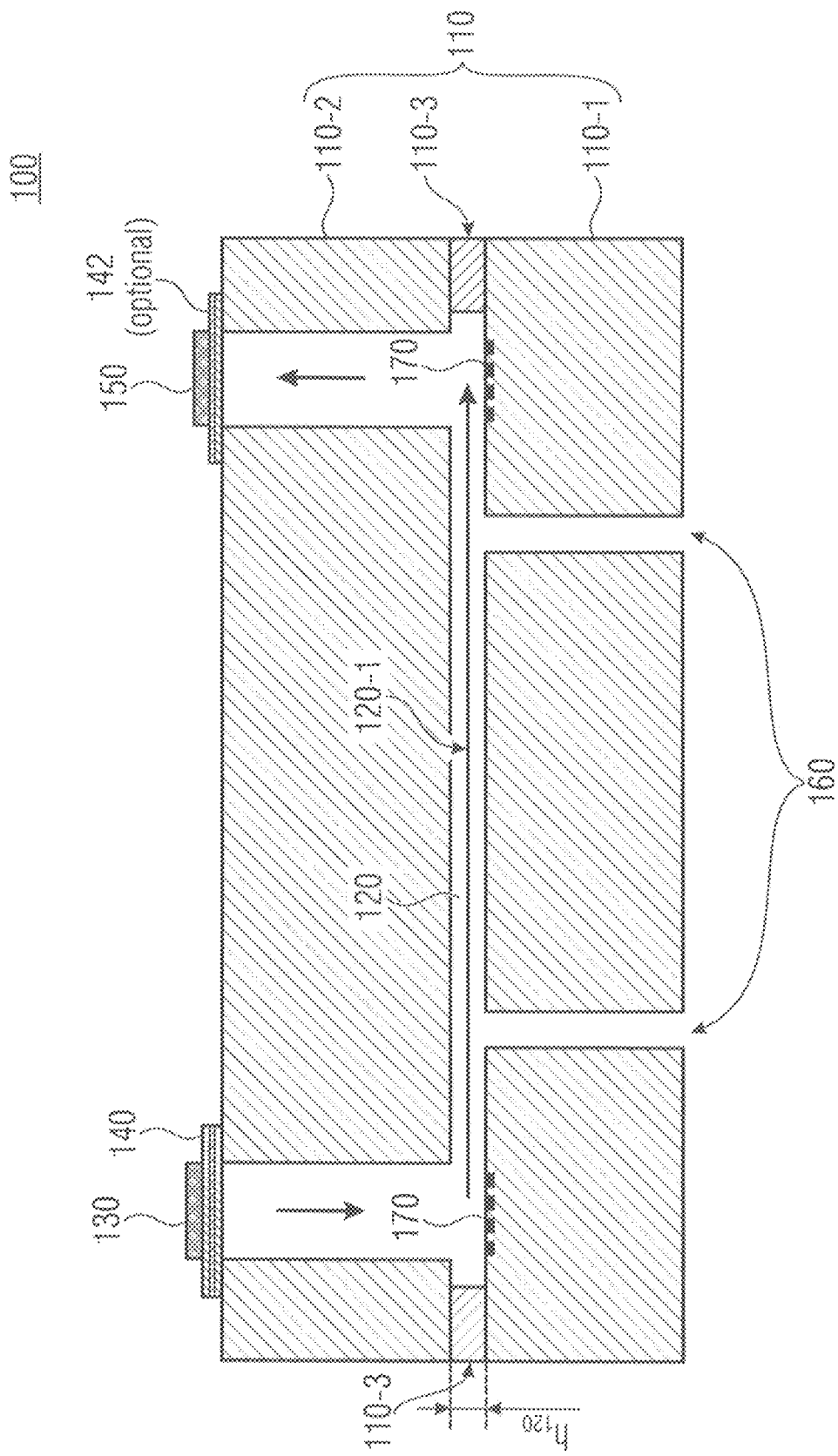
FIG. 3A shows a schematic cross-sectional view of an integrated gas sensor according to a further embodiment.

FIG. 3A shows a schematic cross-sectional view of an integrated gas sensor 100 according to a further embodiment.

As shown in FIG. 3A, the substrate comprises a first partial substrate 100-1 and second partial substrate 110-2 which mechanically bonded together by means a structured spacer element 110-3. The structured spacer element 110-3 is arranged between the first and second partial substrates 110-1, 110-2 for providing the cavity 120 between the mechanically bonded, first and second partial substrates 110-1, 110-2. The structured spacer element 110-3 may be further arranged between the first and second partial substrates 110-1, 110-2 for providing the at least one access hole 160 to the cavity 120. Optionally, at least one of the first and second partial substrates 110-1, 110-2 may comprises the at least one access hole 160 as gas access to the cavity 120.

Figure 3B:
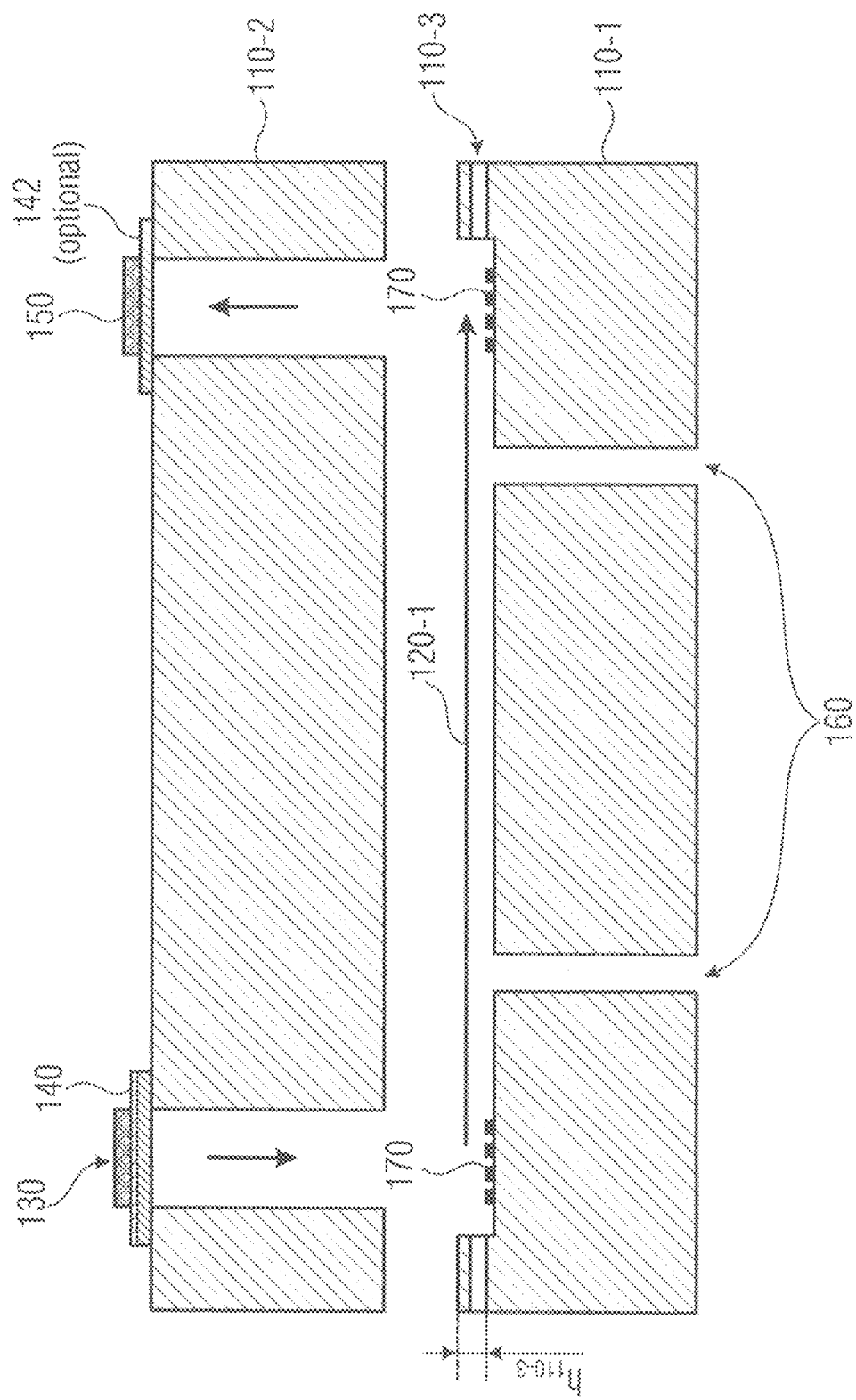
FIG. 3B shows a schematic cross-sectional view of a top wafer and a bottom wafer in a separate condition, e.g., before bonding the two wafers.

FIG. 3B shows a schematic cross-sectional view of a top wafer 110-1 and a bottom wafer 110-2 in a separate condition, e.g. before bonding the two wafers (partial substrates) 110-1, 110-2 to achieve the bonded substrate 110.

According to the integrated gas sensor 100, the cavity 120 may be formed by providing, e.g. depositing, the structured spacer element 110-3 on the first partial substrate 110-1, wherein the structured spacer element 110-3 forms the surrounding walls of the cavity 120. The thickness $h_{110\_3}$ of the structured spacer element 110-3 may be greater than 20 μm or may be between 20 and 100 μm. The thickness $h_{110-3}$ of the structured spacer element 110-3 corresponds to the height $h_{120}$ of the resulting cavity 120. The second partial substrate 110-2 may comprise the source structures 130 and the detector structures 150.

Thus, the cavity 120 may be realized via wafer bonding technology. In this case, the first partial substrate 110-1 may comprise the recess for the cavity 120, which may be generated by depositing the structured spacer element 110-3 on the first partial substrate 110-1. The second partial substrate 110-2 may comprise the source or emitter structures 130 and the detector structures 150. The second partial substrate (top wafer) 110-2 is arranged vertically on top of the first partial substrate (bottom wafer) 110-1. The first partial substrate (top wafer) 110-1 may comprise the grating structures 170 for light deflection, e.g. realized as 50 nm (or between 30 and 70 nm) high lines of poly-silicon with a 2 μm (or a 1 to 3 μm) pitch, for example.

As an alternative approach to the integrated gas sensor 100 of FIG. 1A, the integrated gas sensor 100 of FIG. 2 may be formed by depositing the structured spacer element 110-3 as surrounding walls of the cavity 120 on the first partial substrate 110-1 (and not by a deep etching process).

FIG. 4 shows a schematic cross-sectional view of an integrated gas sensor 100, 100' ac-cording to a further embodiment. The above description with respect to the further elements and structures of the integrated gas sensor 100 of FIGS. 3A-3B is equally applicable to the integrated gas sensor 100 of FIG. 4.

The integrated gas sensor 100 of FIG. 4 further comprises a pair of barrier elements or window elements 180-1, 180-2. The barrier elements 180-1, 180-2 may be arranged to confine and define the sample chamber (or sample volume) 120-1 for the environmental gas. Thus, the cavity path 120-1 is segmented with barrier elements 180-1, 180-2, e.g. two thin Si-"windows", in order to have defined the sample chamber, which is filled with gas. The distance between the barrier elements 180-1, 180-2 defines the resulting length $l_{120-1}$ of the optical interaction path 120-1 (the sample chamber).

The barrier elements 180-1, 180-2 may be transparent for the filter radiation R or for the IR radiation component(s) R, R'. However, the barrier elements (e.g., Si-barriers) 180-1, 180-2 may introduce some reflected light, but, if carefully designed, could also act as optical cavity, which could be used to increase the electric field, and, as a consequence, increase the effective interaction with the analyte.

FIG. 5 shows a schematic cross-sectional view of an integrated gas sensor 100, 100' ac-cording to a further embodiment.

As shown in FIG. 5, the substrate no may comprise a first partial substrate 110-1 and a second partial substrate 110-2, wherein the first partial substrate 110-1 comprises a recess 120 and wherein the second partial substrate 110-2 is formed as a perforated membrane structure covering the recess 120 in the first partial substrate 110-1. The IR emitter 130 and optionally the wavelength selective structure 140 and the IR detector 150 are arranged at the second partial substrate 110-2. The recess 120 in the first partial substrate 110-1 and covered by the second partial substrate 110-2 forms the cavity 120 providing the optical interaction path 120-1. The IR emitter 130 and optionally the wavelength selective structure 140 and the IR detector 150 are optically coupled to the optical interaction path 120-1.

As shown in FIG. 5, the first partial substrate 110-1 and the second partial substrate 110-2 form different parts of the same substrate (single wafer) 110. Thus, the cavity 120 of the integrated gas sensor 100, 100' may be formed in single substrate (single wafer) 110 by using a sacrificial material, wherein processes for fabricating MEMS elements or MEMS microphones can be used.

In the embodiment of FIG. 5, the cavity 120 may be formed by means of a sacrificial layer (carbon or silicon dioxide) which is covered with a polysilicon layer having the access openings 160 that are provided to the sacrificial layer. The cavity 120 is created by removing the sacrificial layer, wherein the emitter 130 and the detector 150 may be arranged on laterally opposite sides of the cavity 120 at access openings 162 to the cavity 120. If the substrate material on which the emitter 130 and detector 150 are located is sufficiently optically transparent, it is not necessary for the openings 162 to be provided through the substrate material to the cavity 120 at the detector 150 and the emitter 130. However, openings are usually provided.

FIGS. 6A-6F show schematic top views (parallel to the x-y-plane) of different possible implementations of the geometry of the cavity 120 for providing the optical interaction path 120-1 of an integrated gas sensor 100, 100' according to further embodiments.

According to embodiments of the present concept, the integrated optical gas sensor 100, 100' comprises a thermal emitter 130, an interaction path 120-1, which is realized as a cavity 120 in the substrate 110, e.g. a silicon substrate, the IR detector element 150 and the wavelength selection element 140, 142.

According to embodiments of the present concept, the cavity 120 for the optical path 120-1 guides the light R essentially in the plane (x-y-plane) of the wafer no from the source 130 to a detector(s) 150, 152. The environmental gas can penetrate the cavity 120 and interact with the radiation R. The lateral dimensions of the cavity 120 should be significantly larger than the wavelength $\lambda_0$. Thus, it is possible to use incoherent radiation $R_0$ from a simple thermal emitter 13o, reducing the complexity of the system, i.e. of the integrated gas sensor 100, 100'.

The interior or inner surfaces 120-A . . . 120-D of the cavity 120 are highly reflective. This can be realized, e.g. with a reflective coating or a metallization of the inner surfaces, e.g. with Au.

Another possible approach to ensure reflectivity may be the use of photonic crystal structures around the cavity 120. Since such structures do not allow propagation at a certain wavelength corresponding to the optical bandgap, this would confine the radiation R in the cavity 120 and, at the same time, provide spectral filtering, because all other wavelengths would be lost.

This filtering effect may also be achieved, if some or all of the surfaces of the cavity are coated with a selective narrow-band reflective coating.

The cavity 120 also comprises some access 160 for the gas. The cavity 120 may have vertical sidewalls (except for the coupling region, see later) and typically features a constant height $h_{120}$ which is larger than the wavelength $\lambda_0$ of the light R. The light R can be guided by standard reflection (in contrast to total internal reflection used in waveguides). The horizontal dimensions of the cavity 120 can be essentially arbitrarily shaped, which provides the means for optimizing the optical path 120-1 in two dimensions, e.g. by including focusing mirrors or other optical elements or by realizing meander structures or spirals to increase the effective path length. This would allow the realization of "2D-Ray Optics", meaning that light can be modelled and controlled in two dimensions and is confined in the $3^{rd}$ dimension by reflection.

FIGS. 6A-6F show exemplary top view of possible structures of the "2D-optical bench".

Figure 6A:
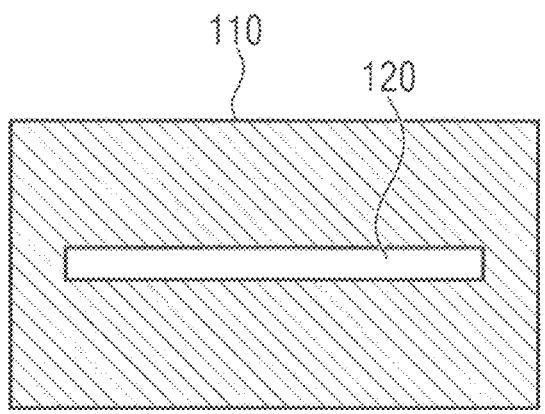
FIGS. 6A-6F show schematic top views of different possible implementations of the geometry of the cavity for providing the optical interaction path according to further embodiments.

As exemplarily shown in FIG. 6A, the cavity 120 forms a linear sample chamber 120-1. A possible way to produce a linear cavity 120 is to provide a groove or recess in a first partial substrate or wafer 110-1, e.g. either by etching or by deposition, and then waver-bonding of the first partial substrate 110-1 to the second partial substrates 110-2, where the emitter 130 and the detector 150 are integrated, to produce the closed cavity 120. However, other procedures and also other geometries are possible. Also other technologies than wafer-bonding might be used for producing the cavity 120, e.g. based on the technologies used in the MEMS microphone fabrication.

Figure 6D:
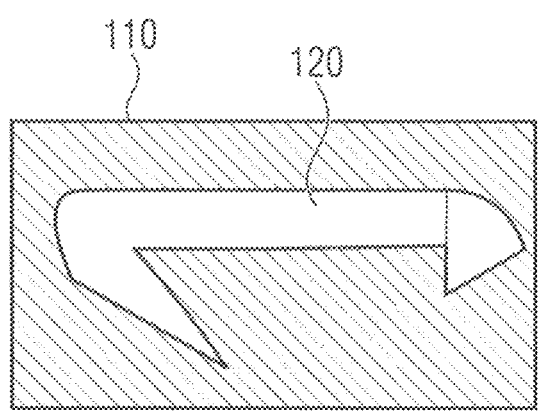
Figure 6B:
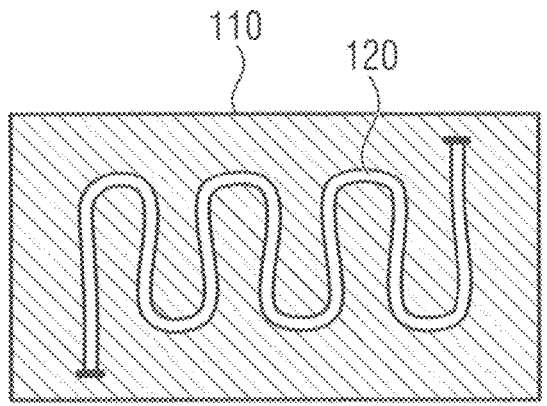

As exemplarily shown in FIG. 6B, the cavity 120 forms a meander type interaction path 120-1.

Figure 6E:
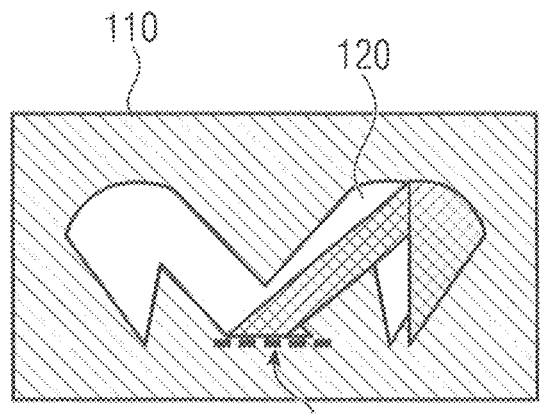
Figure 6C:
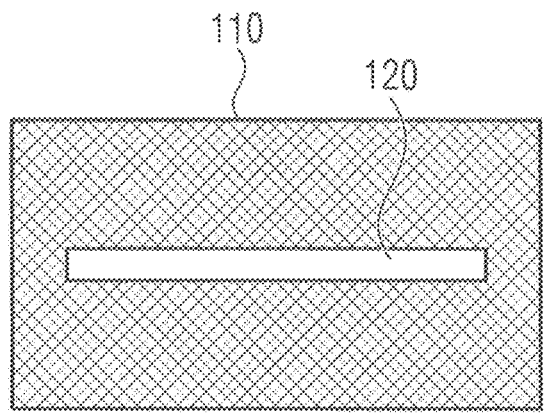

As exemplarily shown in FIG. 6C, a linear cavity 120 is surrounded by a photonic crystal 140.

As exemplarily shown in FIG. 6D, the cavity 120 comprises radiation directing elements 170 in form of deflection structures in the cavity 120 for deflecting or directing the IR radiation R in the optical interaction path 120-1 of the cavity 120 to provide a collimation and/or focusing of the light R onto the detector with a certain horizontal magnification. This enables smaller sources 130.

As exemplarily shown in FIG. 6E, the cavity 120 comprises the incorporation of a grating 170. The grating 170 may allow a separation of spectral components of the IR radiation R.

Figure 6F:
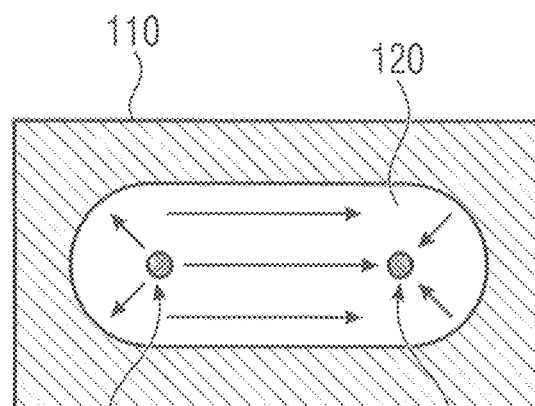

As exemplarily shown in FIG. 6F, the cavity 120 comprises an elliptical shape. The elliptical cavity 120 allows to collect essentially the complete light R from a given point and to focus the light on the detector 150.

Figure 7A:
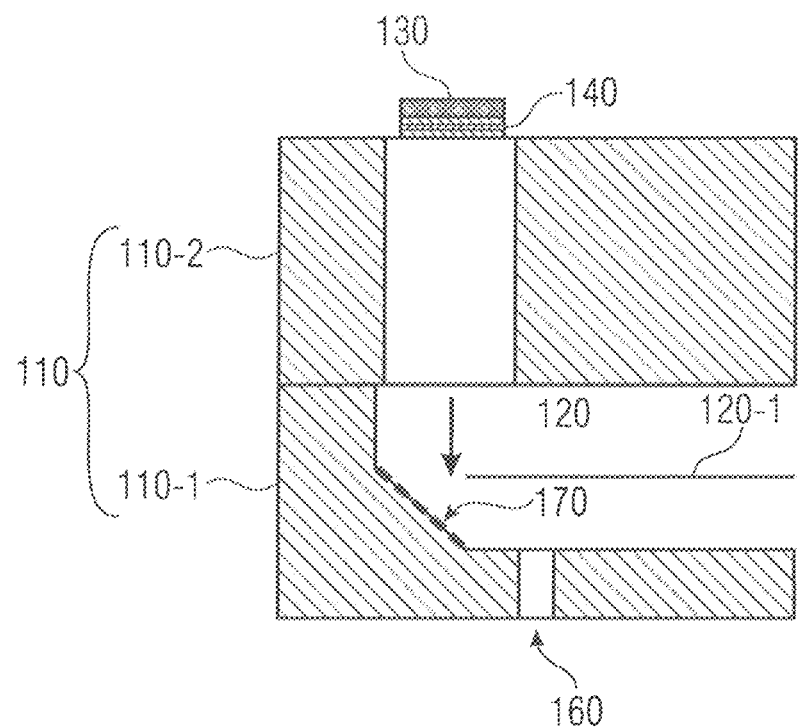
FIGS. 7A-7B show enlarged schematic cross-sectional views of deflection structures of the integrated gas sensor according to further embodiments.
Figure 7B:
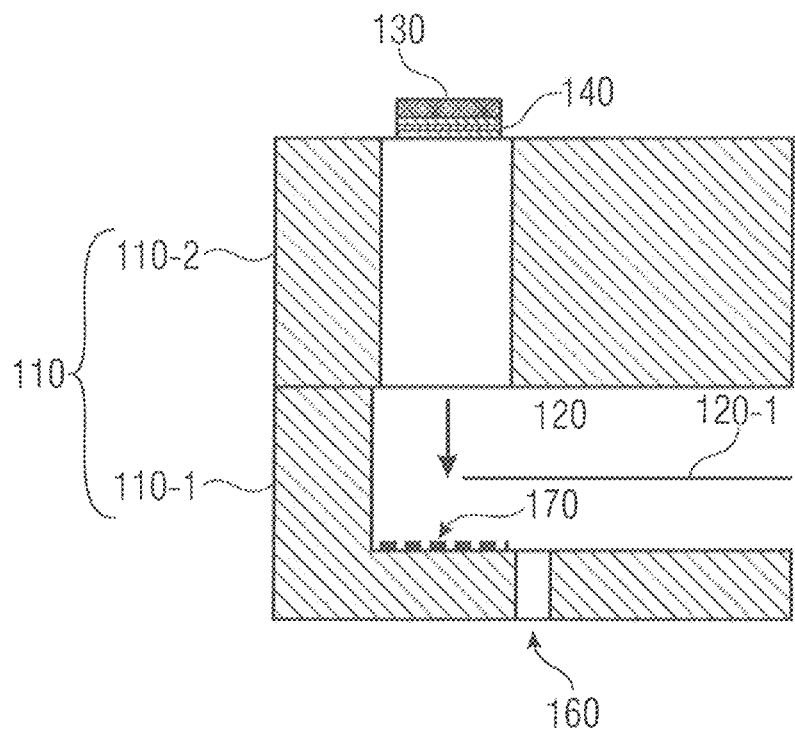

FIGS. 7A-7B show enlarged schematic cross-sectional views of deflection structures or radiation directing elements 170 in the cavity 120 of the integrated gas sensor 100, 100' according to further embodiments. The radiation directing element 170, e.g. a mirror and/or grating, is arranged in the cavity 120 for directing or coupling the filtered IR radiation R into the optical interaction path 120-1 and/or for focusing the filtered IR radiation R to the IR detector 15o, e.g. on the radiation detecting/sensitive surface of the IR detector iso.

A thermal source or emitter can be used the light source 130, which can be implemented, for example, as a conductive region, e.g. a doped Si material or a metallization, etc., which is heated up by applying an electrical current as actuation signal. Typically, there is an optical filter structure 140 in front of the heater 130, in order to filter out the appropriate wavelengths $\lambda_0$ for an interaction with the target gas. An adjustment of the optical bandwidth may also be conducted in front of the detector 130 or somewhere else in the beam-path 120-1. However, filtering directly at the source 130 avoids unnecessary radiation and excess heating of the rest of the cavity 120. The wavelength selective structure 140 can be implemented to filter the emitted radiation $R_0$ as well as to provide a directed and spectrally narrow beam of radiation R. In some cases, the wavelength selective structures 140 are fabricated and arranged within the plane of the substrate (wafer) no and, as a consequence, the radiation R will preferentially be emitted in a direction perpendicular to the direction of the cavity 120.

Thus, the deflection structure 170 is arranged to deflect the beam (radiation R) into the optical interaction path 120-1. As shown in FIG. 7A, the deflection structure 170 can be realized by means of an anisotropic etching process or, as shown in FIG. 7B, by the use of a grating structure. An anisotropic etching process provides a surface region 170 having a tilt angle of e.g., 54.7° (depending on the crystal orientation of the semiconductor substrate no) and a higher efficiency compared to a non-blazed grating. However, an etched deflection structure 170 poses challenges to the cavity design, because it is difficult to ensure the verticality of the cavity side-walls for all directions.

Alternatively, the deflection structure 170 can be realized by means of gratings as shown in FIG. 7B. Similar considerations with respect to the implementation of a further deflection structure 170 apply to the detection part, where the light R, after passing the cavity 120 may be directed to the detector iso.

Thus, FIGS. 7A-7B shows possible schemes to turn the emitted light R by about 90° in order to propagate the light R along the light path 120-1. As shown in FIG. 7A, the deflecting surface 170 with an angle of 54.7° to the x-y-plane is provided, e.g. by means of an anisotropic etching process. As shown in FIG. 7B, the deflecting structure 170 is alternatively provided in form of a grating to deflect the beam R in a defined direction.

According to embodiments of the present concept, essentially any kind of detector 150 can in principle be used as long as the detector 150 is sensitive to the IR wavelength $\lambda_0$. The inexpensive implementation of the detector is a resistor, for example, e.g. in the form of a doped area of a semiconductor, e.g. Si, material, whose resistance changes when it heats up. The possibility of "2D-ray-optics" enables the use of a very small source 130 and/or detector iso, since it becomes possible to collect and refocus the light (at least in 2 dimensions) which provides a greatly enhanced efficiency. A quantum detector 150 may provide a high sensitivity. The same is true for the emission efficiency by means of a quantum emitter 130, like a quantum cascade laser.

According to embodiments of the present concept, a relatively high throughput is expected which enables the use of less sensitive and less complicated detection 150 and emitter 130 schemes.

FIG. 8A shows a schematic cross-sectional view of an integrated gas sensor 100 according to a further embodiment. The above description with respect to FIGS. 1A-1B is equally applicable to the further embodiment of FIG. 8A as described below, wherein the integrated gas sensor 100 of FIG. 8A uses instead the radiation directing elements 170 in form of a grating the deflecting surface 170 with an angle of 54.7° to the x-y-plane, e.g. provided by means of an anisotropic etching process (see also FIG. 7A and the associated description). As shown in FIG. 8A, the gas sensor 100 comprises the radiation directing elements 170, e.g. implemented as mirrors, in the cavity 120 for directing or coupling the filtered IR radiation R into the optical interaction path 120-1 and/or for focusing the filtered IR radiation R to the IR detector 150, e.g. on the radiation detecting/sensitive surface of the IR detector iso.

According to the implementation integrated gas sensor 100 of FIG. 8A, the coupling of the radiation R is achieved with a tilted surface 170, which may be generated using anisotropic etching in Si(1,0,0), for example. The first partial substrate 110-1 comprises the tilted surface 170 so that the radiation R emitted by the heater structure 130 is tilted by about 90° after reflection. This can be implemented by means of a first partial substrate 110-1 having a Si(1,0,0) material, e.g. a Si(1,0,0) wafer.

However, when considering relatively complex sample chamber 120 designs, e.g. corners, meanders, etc., it is also necessary to consider resulting effects and deviations from vertical sidewalls, which may be analyzed on a case to case basis, for example. Nevertheless, in-coupling/out-coupling of the radiation R by means of the tilted surface(s) 170 is expected to be even more efficient when compared to the grating approach (see FIG. 7B, for example).

Figure 8B:
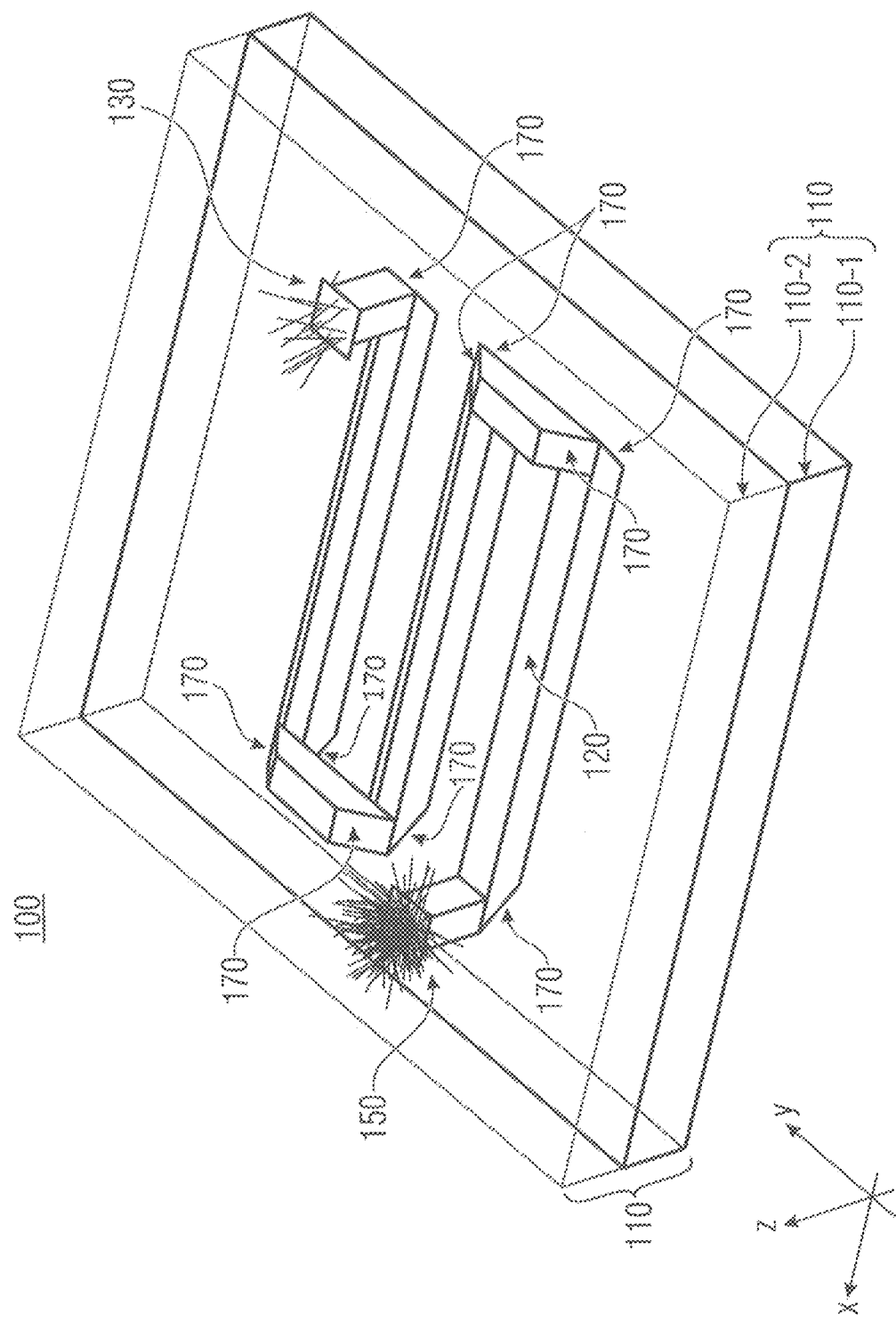
FIG. 8B shows a schematic 3D view of an integrated gas sensor and, especially, of the geometry of the cavity of the integrated gas sensor according to an embodiment.
Figure 9I:
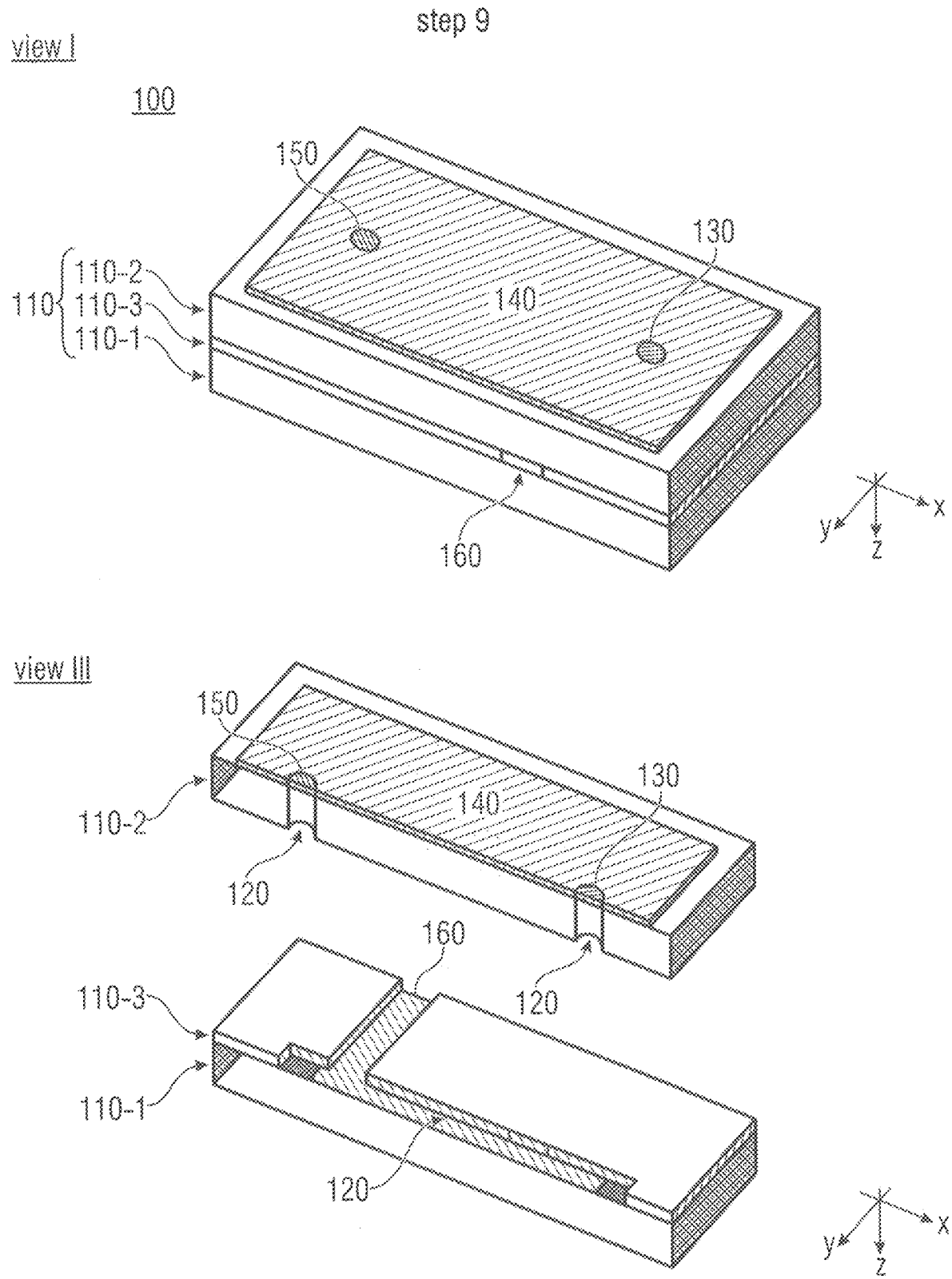

FIG. 8B shows a schematic 3D view of an integrated gas sensor 100 and, especially, of the geometry of a folded cavity 120 of the integrated gas sensor 100 according to an embodiment.

As shown in FIG. 8B, a possible solution for beam-folding may be achieved with anisotropically etched trenches in the semiconductor material of the first and second partial substrates 110-1, 110-2.

The approach with anisotropic etching poses challenges for using more complex structures than a simple linear trench. For example in the case of meander structures for the cavity 120, each turn of the meander structure may feature the tilted surfaces. This may be used for the following implementation approach: Bottom and Top-wafer 110-1, 110-2 would feature only parallel trenches, where the end-walls as deflecting structures 170 are inclined by 54.7° due to the Si(1,0,0) orientation. The wafers 110-1, 110-2 are aligned orthogonally so that a 90° horizontal turn would be implemented by reflecting a beam from a trench in the lower wafer 110-1 up to a trench in the top wafer 110-2, like in a periscope.

FIGS. 9A-9I show schematic 3D top views as schematic snapshots (view I) of the method 200 for manufacturing an integrated gas sensor 100 according to an embodiment.

Moreover, FIGS. 9A-9I show schematic 3D sectional views (view II, III) through a center region of the respective intermediate device along the section line AA and parallel to the x-z-plane during the steps of the method 200 for manufacturing an integrated gas sensor 100 according to an embodiment.

With respect to the method 200 as shown in FIGS. 9A-9I, it is pointed out to the fact that this process flow is one example of multiple ways of how to fabricate the integrated gas sensor 100, wherein the various processing steps can be executed in a different order or combined with additional fabrication steps and/or structuring techniques.

As shown in step 1 of FIG. 9A, a first partial substrate (a plain bottom wafer) 110-1 is provided.

In step 2, grating structures (deflecting structures) 170 are deposited to a first main surface region 110-1A of the first partial substrate 110-1.

In step 3, the structured spacer element 110-3, which defines the cavity 120, is grown on the first main surface region 110-1A of the first partial substrate 110-1. As shown in step 3, the grown structure, i.e. the structured spacer element 110-3, further comprises access holes 160 for the environmental gas comprising the target gas. The access holes 160 are laterally formed in the grown structure 110-3, for example.

In step 4, a metallization 140 is deposited or applied to the exposed surface regions of the cavity 120.

Step 5 additionally shows the provision of a second partial substrate 110-2 (plain top wafer).

In step 6, a wavelength selective structure 140, e.g. a Bragg-filter-structure, is deposited on the first main surface region 110-2A of the second partial substrate 110-2.

In step 7, the thermal emitter (heater) 130 and the IR detector 150 are formed (deposited) on the filter structure 140 on the first main surface region 110-2A of the second partial substrate 110-2.

In step 8, a Bosch etching process for providing the cavity 120 within the partial substrate 110-2 is conducted, wherein a further metallization of the backside 110-2B (second main surface region of the second partial substrate 110-2) of the exposed cavity regions 120 is conducted. Step 8 is only visible in the insides (views II and III) of the FIG. 9H of step 8.

In step 9, a waver bonding process is conducted to bond the first and second partial substrates 110-1, 110-2 to each other wherein at least one of the first and second partial substrates 110-1, 110-2 comprises a recess for providing the cavity 120 between the first and second bonded partial substrates 110-1, 110-1 and for providing the access hole(s) 160 to the cavity 120.

The implementation examples may base on wafer-bonding technology. Also other techniques to create a cavity 120 may be used, e.g. based on MEMS microphone technology. In this case the wafer-bonding step is not necessary.

The basic concept of the integrated gas sensor 100 is to form a cavity 120 in a substrate material 110, e.g. a semiconductor material such as silicon, germanium, or also in a glass wafer or in a substrate made of a silicon dioxide material, wherein the side walls have a sufficiently high reflectivity, e.g. by means of a (vapor-deposited) mirror layer. Any metal such as gold, silver, aluminum, or reflective dielectric materials may be used as materials for the reflective layer covering at least partially the sidewalls of the cavity. Except for the embodiment using a sacrificial material, two substrates/wafers are connected to form the cavity 120 for the interaction of IR radiation/target gas.

According to another embodiment, the sidewalls may also be formed by means of a photonic crystal.

If the access openings 160 are provided in a cover layer as a perforation (hole field), such as in a backplate (for a microphone), the dimensions of the holes may be selected such that they are effective as photonic crystals, and comprise a reflectivity for the IR radiation R coupled in.

In the embodiments in which a bonding process (anodic bonding) is carried out, the substrates, or substrate materials, have to be suitable for this bonding process.

In general, a filter element 140 is provided at the thermal source 130, while a further filter element 142 is optionally provided at the detector 150. A filter element 140, 142 on both sides increases the selectivity for the IR radiation R. The lateral expansion $l_{120}$ of the cavity is in the range of millimeters to centimeters, while the horizontal expansion (height) $h_{120}$ of the cavity 120 is in the range of 5 to 10 μm or ≤200 μm or in the sub-millimeter range.

Additional embodiments and aspects are described which may be used alone or in combination with the features and functionalities described herein.

According to an embodiment, a gas sensor comprises: a substrate having a cavity for providing an optical interaction path for an interaction of a filtered IR radiation having a center wavelength $\lambda_0$ with a target gas in the cavity, wherein the cavity is accessible for an environmental gas comprising the target gas component; a thermal emitter arranged for emitting a broadband IR radiation, wherein the thermal emitter is optically coupled to the cavity; a wavelength selective structure arranged for filtering the broadband IR radiation emitted by the thermal emitter and for providing the filtered IR radiation having the center wavelength $\lambda_0$ in the cavity, wherein the wavelength selective element is optically coupled between the thermal emitter and the cavity, or wherein the wavelength selective element is formed as a bound structure of the cavity; an IR detector arranged to provide a detector output signal based on a signal strength of the filtered IR radiation having traversed the optical interaction path in the cavity and being received by the IR detector.

According to an aspect, the cavity is arranged to provide a length of the optical interaction path which is at least 100 times larger than the center wavelength $\lambda_0$ of the filtered IR radiation, and the part of the cavity forming the optical interaction path is configured to guide the filtered IR radiation having the center wavelength $\lambda_0$ by standard reflection.

According to a further aspect, the substrate comprises at least one access hole to the cavity for providing access of the environmental gas having the target gas component to the cavity.

According to a further aspect, the optical interaction path extends parallel to a bottom sidewall and a top sidewall of the cavity so that the filtered IR radiation is guided along a lateral plane of the substrate.

According to a further aspect, in the gas sensor, a bottom sidewall and a top sidewall of the cavity extend along the optical interaction path parallel to each other for providing an essentially constant height h of the cavity along the optical interaction path, which h is larger than the center wavelength $\lambda_0$.

According to a further aspect, the cavity comprises vertical sidewalls along the optical interaction path.

According to a further aspect, the cavity comprises a meander shape or a spiral shape for providing an accordingly shaped optical interaction path and for providing a resulting length 1 of the optical interaction path which is larger than the lateral dimension of the substrate.

According to a further aspect, the substrate comprises a first partial substrate and a second partial substrate which are bonded to each other, wherein at least one of the first and second partial substrates comprises a recess for providing the cavity between the first and second bonded partial substrates.

According to a further aspect, the gas sensor further comprises a radiation directing element in the cavity for directing the filtered IR radiation into the optical interaction path and/or for focusing the filtered IR radiation to the IR detector.

According to a further aspect, the substrate comprises a first and second partial substrate mechanically bonded together by means of a structured spacer element, wherein the structured spacer element is arranged between the first and second partial substrates for providing the cavity between the mechanically bonded first and second partial substrates.

According to a further aspect, the first partial substrate comprises a recess and the second partial substrate is formed as a perforated membrane structure covering the recess in the first partial substrate, wherein the IR emitter (and optionally the wavelength selective structure) and the IR detector are arranged at the second partial substrate.

According to a further aspect, the IR emitter comprises a conductor having a main emission surface region for emitting a broadband IR radiation in a main radiation emission direction.

According to a further aspect, the conductor comprises a highly-doped semiconductor strip, wherein a metallic cover layer at least partially covers the main emission surface region of the semiconductor strip.

According to a further aspect, the main radiation emission direction of the IR emitter is angularly offset to a lateral extension plane of the cavity, the gas sensor further comprising a deflection structure in the cavity for deflecting the filtered IR radiation into the optical interaction path in the cavity.

According to a further aspect, the wavelength selective structure is formed as an optical band-pass filter structure having a narrow transmission band for providing the filtered IR radiation having the center wavelength $\lambda_0$.

According to a further aspect, the wavelength selective structure comprises at least one of a filter structure between the IR emitter and the cavity, a photonic crystal structure in lateral sidewall regions of the cavity, and a wavelength selective coating of inner wall regions of the cavity, for providing the filtered (narrowband) IR radiation having the center wavelength $\lambda_0$ in the cavity.

According to a further aspect, the IR detector comprises a resistive temperature sensor, a pyroelectric temperature sensor, a piezoelectric temperature sensor or a pn junction temperature sensor, which is configured to provide a detector output signal based on a signal strength of the filtered IR radiation propagated through the optical interaction path of the cavity and is incident on the IR detector.

According to a further aspect, the IR detector is configured to sense the strength of the incident filtered IR radiation which is a measure of the concentration of the target gas in the cavity.

According to an embodiment, a gas sensor comprises: a substrate having a cavity for providing an optical interaction path for an interaction of an IR radiation component with a target gas in the cavity, wherein the cavity is accessible for an environmental gas comprising the target gas; a thermal emitter arranged for emitting a broadband IR radiation having the IR radiation component, wherein the thermal emitter is optically coupled to the cavity; an IR detector arranged to provide a detector output signal based on a signal strength of the IR radiation component having traversed the optical interaction path in the cavity and being received by the IR detector; and a wavelength selective structure arranged for filtering the broadband IR radiation emitted by the thermal emitter, wherein the wavelength selective element is optically coupled between the cavity and the IR detector for providing a filtered IR radiation comprising the IR radiation component having the center wavelength $\lambda 0$ to the IR detector.

According to an aspect, the gas sensor further comprises: a further IR detector arranged to provide a detector output signal based on a signal strength of the IR radiation having traversed the optical interaction path in the cavity and being received by the IR detector; and a further wavelength selective structure arranged for filtering the broadband IR radiation emitted by the thermal emitter, wherein the wavelength selective element is optically coupled between the cavity and the further IR detector for providing a filtered IR radiation comprising a further IR radiation component having a further center wavelength $\lambda_1$ to the further IR detector.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

In the foregoing Detailed Description, it can be seen that various features are grouped together in examples for the purpose of streamlining the disclosure. This method of disclosure is not to be interpreted as reflecting an intention that the claimed examples require more features than are expressly recited in each claim. Rather, as the following claims reflect, subject matter may lie in less than all features of a single disclosed example. Thus the following claims are hereby incorporated into the Detailed Description, where each claim may stand on its own as a separate example.

While each claim may stand on its own as a separate example, it is to be noted that, although a dependent claim may refer in the claims to a specific combination with one or more other claims, other examples may also include a combination of the dependent claim with the subject matter of each other dependent claim or a combination of each feature with other dependent or independent claims. Such combinations are proposed herein unless it is stated that a specific combination is not intended. Furthermore, it is intended to include also features of a claim to any other independent claim even if this claim is not directly made dependent to the independent claim.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that the embodiments be limited only by the claims and the equivalents thereof.

What is claimed is:

1. A gas sensor, comprising:
   a substrate having a cavity for providing an optical interaction path for an interaction of a filtered IR radiation having a center wavelength $\lambda_0$ with a target gas in the cavity, wherein the cavity is accessible for an environmental gas comprising the target gas;
   a thermal emitter configured to emit broadband IR radiation, wherein the thermal emitter is optically coupled to the cavity;
   a wavelength selective structure configured to filter the broadband IR radiation emitted by the thermal emitter and configure to provide the filtered IR radiation having the center wavelength $\lambda_0$ in the cavity, wherein the wavelength selective structure is optically coupled between the thermal emitter and the cavity, or the wavelength selective structure is formed as a bound structure of the cavity;
   an IR detector configured to provide a detector output signal based on a strength of the filtered IR radiation having traversed the optical interaction path in the cavity and being received by the IR detector; and
   a radiation directing element affixed and parallel to a surface of the cavity for directing the filtered IR radiation into the optical interaction path or for focusing the filtered IR radiation to the IR detector, wherein the radiation directing element comprises a grating structure.

2. The gas sensor of claim 1, wherein the cavity is arranged to provide a length of the optical interaction path which is at least wo times larger than the center wavelength $\lambda_0$ of the filtered IR radiation, and wherein a portion of the cavity forming the optical interaction path is configured to guide the filtered IR radiation having the center wavelength $\lambda_0$ by standard reflection.

3. The gas sensor of claim 1, wherein the substrate comprises at least one access hole to the cavity for providing access of the environmental gas having the target gas to the cavity.

4. The gas sensor of claim 1, wherein the optical interaction path extends parallel to a bottom sidewall and a top sidewall of the cavity so that the filtered IR radiation is guided along a lateral plane of the substrate.

5. The gas sensor of claim 1, wherein a bottom sidewall and a top sidewall of the cavity extend along the optical interaction path parallel to each other for providing a constant height of the cavity along the optical interaction path, which is larger than the center wavelength $\lambda_0$.

6. The gas sensor of claim 1, wherein the cavity comprises vertical sidewalls along the optical interaction path.

7. The gas sensor of claim 1, wherein the cavity comprises a meander shape or a spiral shape for providing an accordingly shaped optical interaction path and for providing a resulting length of the optical interaction path which is larger than a lateral dimension of the substrate.

8. The gas sensor of claim 1, wherein the substrate comprises a first partial substrate and a second partial substrate that are bonded to each other, wherein at least one of the first partial substrate or the second partial substrate comprises a recess for providing the cavity between the first and second bonded partial substrates.

9. The gas sensor of claim 1, wherein the substrate comprises a first partial substrate and a second partial substrate mechanically bonded together, wherein a structured spacer element is arranged between the first and second partial substrates for providing the cavity between the mechanically bonded first and second partial substrates.

10. The gas sensor of claim 9, wherein the first partial substrate comprises a recess and wherein the second partial substrate is formed as a perforated membrane structure covering the recess in the first partial substrate, wherein the thermal emitter and the IR detector are arranged at the second partial substrate.

11. The gas sensor of claim 1, wherein the thermal emitter comprises a conductor having a main emission surface region for emitting a broadband IR radiation in a main radiation emission direction.

12. The gas sensor of claim 11, wherein the conductor comprises a highly-doped semiconductor strip, wherein a metallic cover layer at least partially covers the main emission surface region of the semiconductor strip.

13. The gas sensor of claim 11, wherein:
   the main radiation emission direction of the thermal emitter is angularly offset to a lateral extension plane of the cavity; and
   the gas sensor further comprises a deflection structure in the cavity for deflecting the filtered IR radiation into the optical interaction path in the cavity.

14. The gas sensor of claim 1, wherein the wavelength selective structure is formed as an optical band-pass filter structure having a narrow transmission band for providing the filtered IR radiation having the center wavelength $\lambda_0$.

15. The gas sensor of claim 1, wherein the wavelength selective structure comprises at least one of a resonator structure between the thermal emitter and the cavity, a photonic crystal structure in lateral sidewall regions of the cavity or a wavelength selective coating of inner wall regions of the cavity for providing the filtered IR radiation having the center wavelength $\lambda_0$ in the cavity.

16. The gas sensor of claim 1, wherein the IR detector comprises a resistive temperature sensor, a pyroelectric temperature sensor, a piezoelectric temperature sensor or a pn junction temperature sensor, which is configured to provide a detector output signal based on a strength of the filtered IR radiation propagated through the optical interaction path of the cavity and incident on the IR detector.

17. The gas sensor of claim 1, wherein the IR detector is configured to sense a strength of the filtered IR radiation incident on the IR detector, wherein the sensed strength is a measure of a concentration of the target gas in the cavity.

18. A gas sensor, comprising:
   a substrate having a cavity configured to provide an optical interaction path for an interaction of an IR radiation component with a target gas in the cavity, wherein the cavity is accessible for an environmental gas comprising the target gas;

a thermal emitter configured to emit a broadband IR radiation having the IR radiation component, wherein the thermal emitter is optically coupled to the cavity;

a first IR detector configured to provide a first detector output signal based on a strength of the IR radiation component having traversed the optical interaction path in the cavity and being received by the first IR detector;

a first wavelength selective structure configured to filter the broadband IR radiation emitted by the thermal emitter, wherein the first wavelength selective structure is optically coupled between the cavity and the first IR detector for providing a first filtered IR radiation comprising the IR radiation component having a first center wavelength $\lambda_0$ to the first IR detector; and a radiation directing element affixed and parallel to a surface of the cavity for directing the filtered IR radiation into the optical interaction path or for focusing the filtered IR radiation to the IR detector, wherein the radiation directing element comprises a plurality of polysilicon lines.

19. The gas sensor of claim 18, further comprising:

a second IR detector; and a second wavelength selective structure configured to filter the broadband IR radiation emitted by the thermal emitter, wherein the second wavelength selective structure is optically coupled between the cavity and the second IR detector for providing a second filtered IR radiation comprising a second IR radiation component having a second center wavelength $\lambda_1$ to the second IR detector, wherein the second IR detector is configured to provide a second detector output signal based on a strength of the second filtered IR radiation having traversed the optical interaction path in the cavity and being received by the second IR detector.

20. A method, comprising:

emitting a broadband IR radiation using a thermal emitter optically coupled to a cavity disposed in a substrate;

filtering the broadband IR radiation using a wavelength selective structure optically coupled between the thermal emitter and the cavity to provide filtered IR radiation, wherein the filtered IR radiation has a center wavelength $\lambda_0$ with a target gas in the cavity;

using an IR detector, detecting the filtered broadband IR radiation after the filtered broadband IR radiation traverses an optical interaction path within the cavity; and affixing a radiation directing element parallel to a surface of the cavity for directing the filtered IR radiation into the optical interaction path or for focusing the filtered IR radiation to the IR detector, wherein the radiation directing element comprises a grating structure.

* * * * *